US008901164B2

(12) United States Patent
Fletcher

(10) Patent No.: US 8,901,164 B2
(45) Date of Patent: Dec. 2, 2014

(54) AMPHIPATHIC AND OTHER DOUBLE-SIDED ALPHA-HELIX MIMETICS BASED ON A 1,2-DIPHENYLACETYLENE SCAFFOLD

(71) Applicant: University of Maryland, Baltimore, Baltimore, MD (US)

(72) Inventor: Steven Fletcher, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 14/200,774

(22) Filed: Mar. 7, 2014

(65) Prior Publication Data

US 2014/0256817 A1 Sep. 11, 2014

Related U.S. Application Data

(60) Provisional application No. 61/774,162, filed on Mar. 7, 2013.

(51) Int. Cl.
*A61K 31/395* (2006.01)
*C07D 498/00* (2006.01)
*C07C 237/34* (2006.01)
*C07C 237/30* (2006.01)

(52) U.S. Cl.
CPC ............ *C07C 237/34* (2013.01); *C07C 237/30* (2013.01)
USPC .......................................... 514/450; 540/468

(58) Field of Classification Search
USPC .......................................... 540/468; 514/450
See application file for complete search history.

(56) References Cited

PUBLICATIONS

Cary et al., Hydrogen Bond-Stabilized Helix Formation of a m-Phenylene Ethynylene Oligomer, 2002, Organic Letters, vol. 4, No. 26, 4663-4666.*
Adams, J. M. et al. The Bcl-2 Protein Family: Arbiters of Cell Survival, *Science*, 1998, 281, 1322-1326.
Allen, M.P. et al. *Computer Simulation of Liquids*; Clarendon Press: Oxford, 1987.
Azzarito, V. et al. Inhibition of α-helix-mediated protein-protein interactions using designed molecules, *Nat. Chem.*, 2013, 5, 161-173.
Barlow, D. J. et al. Helix Geometry in Proteins. *J. Mol. Biol.*, 1988, 201, 601-619.
Boersma, M. D. et al. Hydrophile scanning as a complement to alanine scanning for exploring and manipulating protein-protein recognition: Application to the Bim BH3 domain, *Protein Sci.*, 2008, 17, 1232-1240.
Bouvier, M. et al. Probing the Functional Conformation of Neuropeptide Y through the Design and Study of Cyclic Analouges, *J. Med. Chem.*, 1992, 35, 1145-1155.
Brooks, B.R. et al. CHARMM: The Biomolecular Simulation Program, *J. Comput. Chem*. 2009, 30, 1545-1614.
Bullock, B.N. et al. Assessing Helical Protein Interfaces for Inhibitor Design, *J. Am. Chem. Soc.*, 2011, 133, 14220-14223.
Cary, J. M. et al. Hydrogen Bond-Stabilizing Helix Formation of a m-Phenylene Ethynylene Oligomer, *Org. Lett.*, 2002, 4, 4663-4666.
Cornette, J.L. et al. Hydrophobicity Scales and Computational Techniques for Detecting Amphipathic Structures in Proteins, *J. Mol. Biol.*, 1987, 195, 659-685.
Cummings, C.G. et al. Synthesis and Biological Evaluation of a 5-6-5 Imidazole-Phenyl-Thiazole Based α-helx Mimetic, *Org. Lett.*, 2009, 11, 25-28.
Cummings, C.G. et al. Disrupting protein-protein interactions with non-peptic, small molecule α-helix mimetics, *Curr. Opin. Chem. Biol.*, 2010, 14, 341-346.
Czabotar, P.E. et al. Structural insights into the degradation of Mcl-4 induced by BH3 domains, *Proc. Natl. Acad. Sci. USA* 2007, 104, 6217-6222.
Darden, T.A. et al. Particle mesh Ewald: an $N \cdot \log(N)$ method for Ewald sums in large systems, *J. Chem. Phys.*, 1993, 98, 10089-10092.
Davis, J. M. et al. Synthesis of a 2,3';6', 3—Terpyridine Scaffold as an α-Helix Mimetic, *Org. Lett.*, 2005, 7, 5405-5408.
Ernst, J.T. et al. Design of a Protein Surface Antagonist Based on a α-Helix Mimnicry: Inhibition of gp41 Assembly and Viral Fusion, *Angew. Chem. Int. Ed.*, 2002, 41, 278-281.
Ernst, J.T. et al. Design and Application of an α-Helix-Mimetic Scaffold Based on an Oligoamide-Foldamer Strategy: Antagonisam of the Bak BH3/Bcl-xL Complex, *Angew. Chem. Int. Ed.*, 2003, 42, 535-539.
Feller, S.E. et al. Constant pressure molecular dynamics simulation: The Langevin piston method, *J. Chem. Phys.*, 1995, 103, 4613-4621.
Fletcher, S. et al. Protein surface recognition and proteomimetics: mimcs of protein surface structure and function, *Curr. Opin. Chem. Biol.*, 2005, 9, 632-638.
Hockney, R.W. In *Methods in Computational Physics*; Academic Press: New York, 1970, p. 136-211.
Hoover, W. G. Canonical dynamics: Equilibrium phase-space distributions, *Phys. Rev. A*, 1985, 31, 1695-1697.
Horne, S.W. et al. Foldamers with Heterogeneous Backbones, *Acc. Chem. Res.*, 2008, 41,1399-1408.
Jackson, D. Y. et al. General Approach to the Synthesis of Short α-Helix Peptides, *J. Am. Chem. Soc.*, 1991, 113, 9391-9392.
Jansma, A. et al. Verification of a Designed Intramolecular Hydrogen Bond in a Drug Scaffolding by Nuclear Magnetic Resonance Spectroscopy, *J. Med. Chem.* 2007, 50, 5875-5877.
Marimganti, S. et al. Novel Amphiphilic α-Helix Mimetics Based on a Bis-benzamide Scaffold, *Org. Lett.*, 2009, 11, 4418-4421.
Marqusee, S. et al. Helix stabilization by Glu⁻ ••• Lys and R. L. Baldwin, *Proc. Natl. Acad. Sci. USA*, 1987, 84, 8898-8902.
Nosé, S. A molecular dynamics method for simulations in the canonical ensemble, *Mol. Phys.*, 1984, 52, 255-268.

(Continued)

*Primary Examiner* — Kristin Vajda
(74) *Attorney, Agent, or Firm* — Marianne Fuierer; Moore & Van Allen, PLLC

(57) ABSTRACT

Small-molecule scaffolds based on 1,2-diphenylacetylene that accurately replicate the spatial and angular projections of several side chains on both faces of an α-helix, specifically the i and i+7 side chains on one face, and the i and i+2 side chains on the other. The amphipathic α-helix mimetic can be used to disrupt disease-promoting protein-protein interactions that are mediated by α-helices.

11 Claims, 7 Drawing Sheets

(56) References Cited

PUBLICATIONS

Plante, J. et al. Synthesis of functional aromatic oligamide rods, *Org. Biomol. Chem.*, 2008, 6, 138-146.

Ryckaert, J.P. et al. Numerical Integration of the Cartesan Equations of Motion of a System with Constraints: Molecular Dyanmaiucs of n-Alkanes, *J. Comput. Phys.*, 1977, 23, 327-341.

Schafmeister, C.E. et al. An All-Hydrocarbon Cross-Linking System for Enhancing the Helicity and Metabolic Stability of Peptides, *J. Am. Chem. Soc.*, 2000, 122, 5891-5892.

Schneider, J.P. et al. Templates Thant Induce α-Hleical, β-Sheet, and Loop Confirmation, *Chem. Rev.*, 1995, 95, 2169-2187.

Steinbach, P. J. et al New Spherical-Cutoff Methods for Long-Range Forces in Macromolecular Simulation, *J. Comput. Chem.*, 1994, 15, 667-683.

Thompson, S. et al. Double-sided α-helix mimetics, *Tetrahedron*, 2012, 68, 4501-4505.

Vanommeslaeghe, K. et al. CHARMM General Force Field: A Force Filed for Drug-Like Molecules Compatible with the CHARMM All-Atom Additive Biological Force Fields, *J. Comput. Chem.*, 2010, 31, 671-690.

Vanommeslaeghe, K. et al. Automation of the CHARMM General Force Field (CGenFF) I: Bond Perception and Atom Typing, *J. Chem. Inf. Model.*, 2012, 52, 3144-3154.

Vanommeslaeghe, K. et al. Automation of the CHARMM General Force Field (CGenFF) II: Assignment of Bonded Parameters and Partial Atomic Charges, *J. Chem. Inf. Model.*, 2012, 52, 3155-3168.

Volonterio, A. et al. Synthesis of Pyridazine-Based Scaffolds as a α-Helix Mimetics, *Org. Lett.*, 2007, 9, 3733-3736.

Wagner, G. et al. Hydrogen Bond Length and [1] H NMR Chemical Shifts in Proteins, *J. Am. Chem. Soc.*, 1983, 105, 5948-5949.

Wyrembak, P. N. et al. Alkyne-Linked 2,2-Distributed-Indolin-3-on3 Oligomers as Extended β-Strand Mimetics, *J. Am. Chem. Soc.*, 2009, 131, 45664567.

Yap, J. L. et al. Relaxation of the rigid backbone of an oligoamide-foldamer-based α-helix mimetic: identificatin of potent $Bcl-x_L$ inhibitors, *Org. Biomol. Chem.*, 2012, 10, 2928-2933.

Yin, H. et al. Terephthalamide Derivatives as Mimetics of Helical Peptides: Disruption of the $Bcl-x_L$/Bak Interacation, *J. Am. Chem. Soc.*, 2005, 127, 54635468.

Youle, R. J. et al. The BCL-2 protein family: opposing activities that medate cell death, *Nat. Rev. Mol. Cell Biol.*, 2008, 9, 47-59.

Zhang, Z, et al. An Anthraquinone Scaffold for Putative, Two-Face BH3 α-Helix Mimic, *J. Med. Chem.* 2012, 55, 10735-10741.

\* cited by examiner

AMPHIPATHIC AND OTHER DOUBLE-SIDED ALPHA-HELIX MIMETICS BASED ON A 1,2-DIPHENYLACETYLENE SCAFFOLD

CROSS REFERENCE TO RELATED APPLICATIONS

This application claims priority to U.S. Provisional Patent Application No. 61/774,162 filed Mar. 7, 2013 in the name of Steven Fletcher entitled "Amphipathic and Other Double-Sided Alpha-Helix Mimetics Based on a 1,2-Diphenylacetylene," which is incorporated by reference herein in its entirety.

FIELD

The present invention generally relates to a small-molecule scaffold that substantially replicates the spatial and angular projections of several side chains on both faces of an α-helix. The amphipathic α-helix mimetic can be used to disrupt disease-promoting protein-protein interactions that are mediated by α-helices.

BACKGROUND

α-Helices are the most common form of protein secondary structure [1], and they play critical roles in mediating a diverse array of protein-protein interactions (PPIs) that include signal transduction, transcription, apoptosis, and immune responses [2]. Molecules that can reproduce the spatial and angular projections of key side chains of α-helices are of interest as novel biochemical tools and/or new leads for drug discovery [3]. Exhibiting random coil in solution and prone to metabolic degradation, short peptides themselves, however, do not represent attractive leads [4]. Instead, several alternative strategies towards effective mimicry of the α-helix have been adopted, which include the introduction of side chain constraints into peptides, such as salt [5], lactam [6] and disulfide [7] bridges. An especially noteworthy application of this approach is manifested in the "hydrocarbon stapled" α-helices in which olefin metathesis between unnatural amino acid side chains "locks" the peptide into the desired α-helical conformation [8]. β-peptide foldamers that fold into helical structures have also been described [9]. Pre-organization not only increases binding affinity to target proteins but also improves metabolic stability [8].

Complementary to these peptidomimetic approaches, Hamilton previously pioneered a proteomimetic strategy, in which small-molecule, non-peptidic scaffolds are suitably decorated to accomplish mimicry of the spatial and angular projections of key side chains of α-helices [10]. The original α-helix mimetic scaffold described by Hamilton is the terphenyl scaffold [11], which has inspired a wide range of related frameworks, including a variety of five and six-membered heterocycles [12], derivatives of terephthalic acid [13], as well as tris-picolinamides [14] and tris-benzamides [15], and combinations thereof [16]. Until recently, synthetic α-helix mimicry focused on replication of only the hydrophobic face of the α-helix, typically the i, i+3/4 and i+7 residues. Rebek and Hamilton later introduced α-helix mimetics in which heteroatoms were incorporated into the opposite face of the scaffold to improve aqueous solubility [17]. Around 50% of the α-helices that are found in proteins are amphipathic, presenting both a hydrophobic face and a hydrophilic face [18].

It is of interest, therefore, to develop synthetic α-helix mimetics that can mimic both faces of an α-helix, as this may enhance the binding affinity of the synthetic ligand as well as improve its selectivity profile. Elaboration of previously-reported α-helix mimetic scaffolds has allowed for mimicry of both faces of the α-helix [19]. Novel and diverse amphipathic α-helix mimetic scaffolds would be welcomed to enhance the pool of potential leads for drug discovery.

SUMMARY

The present invention generally relates to a small-molecule scaffold that substantially replicates the spatial and angular projections of several side chains on both faces of an α-helix, specifically the i and i+7 side chains on one face, and the i and i+2 side chains on the other. The small-molecule scaffold described herein permits the mimicry of a fifth amino acid side chain, allowing for even stronger binding interactions with its target protein. As a result of the binding interactions, the amphipathic α-helix mimetic can be used to disrupt disease-promoting protein-protein interactions that are mediated by α-helices, for example, Bak-Bcl-$x_L$, Bim-Mcl-1, c-Myc-Max, c-Jun-Fos, p53-HDM2, and the like.

In one aspect, a compound of formulas 1a-1c is described:

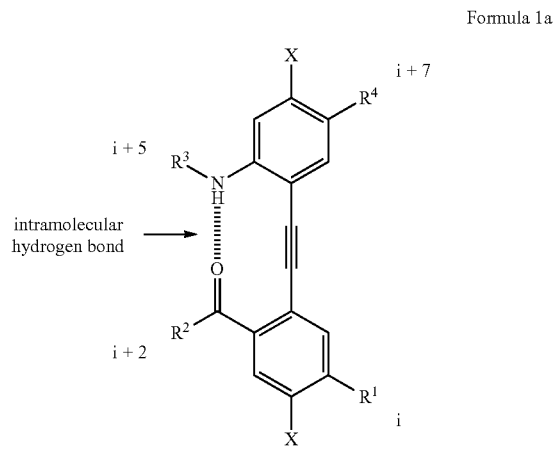

Formula 1a

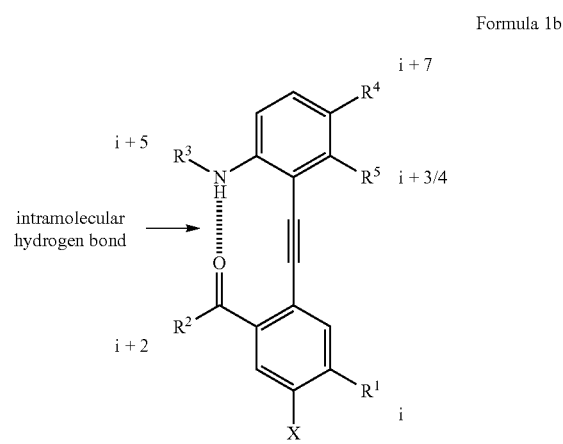

Formula 1b

Formula 1c

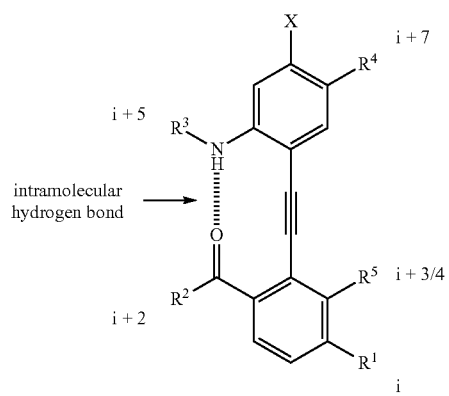

wherein:
R¹, R⁴, R⁵ can be alkyl, cycloalkyl, alkenyl, alkynyl, aryl, $CH_2$-aryl, heteroaryl, $CH_2$-heteroaryl, $CH_2CO_2H$, $CH_2CH_2CO_2H$, $CH_2OH$, $(CH_2)_4NH_2$, $(CH_2)_3N=C(NH_2)_2$, O-alkyl, O-cycloalkyl, O-alkenyl, O-alkynyl, O-aryl, O—$CH_2$-aryl, O-heteroaryl, O—$CH_2$-heteroaryl, O—$CH_2CO_2H$, O—$CH_2CH_2CO_2H$, O—$(CH_2)_2OH$, O—$(CH_2)_4NH_2$, O—$(CH_2)_3N=C(NH_2)_2$;
R² can be alkyl, cycloalkyl, alkenyl, alkynyl, aryl, $CH_2$-aryl, heteroaryl, $CH_2$-heteroaryl, O-alkyl, O-cycloalkyl, O-alkenyl, O-alkynyl, O-aryl, O—$CH_2$-aryl, O-heteroaryl, O—$CH_2$-heteroaryl, NH-alkyl, NH-cycloalkyl, NH-alkenyl, NH-alkynyl, NH-aryl, NH—$CH_2$-aryl, NH-heteroaryl, NH—$CH_2$-heteroaryl, CO-alkyl, CO-cycloalkyl, CO-alkenyl, CO-alkynyl, CO-aryl, CO—$CH_2$-aryl, CO-heteroaryl, CO—$CH_2$-heteroaryl, $CO_2$-alkyl, $CO_2$-cycloalkyl, $CO_2$-alkenyl, $CO_2$-alkynyl, $CO_2$-aryl, $CO_2$—$CH_2$-aryl, $CO_2$-heteroaryl, $CO_2$—$CH_2$-heteroaryl;
R³ can be alkyl, cycloalkyl, alkenyl, alkynyl, aryl, $CH_2$-aryl, heteroaryl, $CH_2$-heteroaryl, CO-alkyl, CO-cycloalkyl, CO-alkenyl, CO-alkynyl, CO-aryl, CO—$CH_2$-aryl, CO-heteroaryl, CO—$CH_2$-heteroaryl, $CO_2$-alkyl, $CO_2$-cycloalkyl, $CO_2$-alkenyl, $CO_2$-alkynyl, $CO_2$-aryl, $CO_2$—$CH_2$-aryl, $CO_2$-heteroaryl, $CO_2$—$CH_2$-heteroaryl, $COCO_2H$, $COCO_2$-alkyl, $COCO_2$-cycloalkyl, $COCO_2$-alkenyl, $COCO_2$-alkynyl, $COCO_2$-aryl, $COCO_2$—$CH_2$-aryl, $COCO_2$-heteroaryl, $COCO_2$—$CH_2$-heteroaryl, $SO_2$-alkyl, $SO_2$-cycloalkyl, $SO_2$-alkenyl, $SO_2$-alkynyl, $SO_2$-aryl, $SO_2$—$CH_2$-aryl, $SO_2$-heteroaryl, $SO_2$—$CH_2$-heteroaryl; and
X=H, $OCH_2CO_2H$, wherein the latter functionality serves as a solubilizing group.

In another aspect, a compound of formula 2 is described:

Formula 2

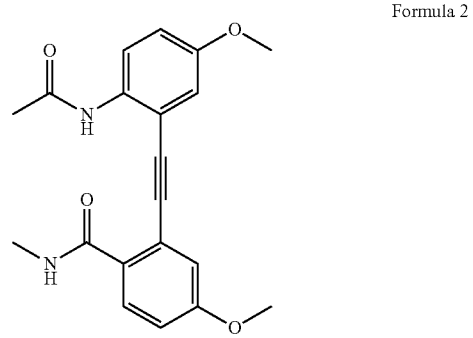 [SMILES: CNC(=O)c1ccc(OC)cc1C#Cc1cc(OC)ccc1NC(C)=O]

In still another aspect, a compound of formula 14 is described:

Formula 14

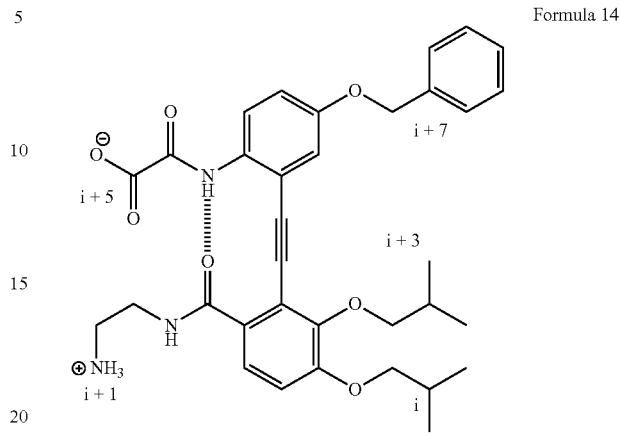

In yet another aspect, a method of disrupting disease-promoting protein-protein interactions that are mediated by α-helices is described, said method comprising interacting a compound of formulas 1a-1c with a protein such that the protein-protein interactions are antagonized and the disease promotion is disrupted, wherein the disease-promoting protein-protein interactions are selected from the group consisting of Bim-Mcl-1, c-Myc-Max, c-Jun-Fos, and p53-HDM2.

In still another aspect, a pharmaceutical composition is described, said pharmaceutical composition comprising a compound of formulas 1a-1c and a pharmaceutically acceptable excipient.

Other aspects, features and advantages of the invention will be more fully apparent from the ensuing disclosure and appended claims.

DETAILED DESCRIPTION

Figure 1A:
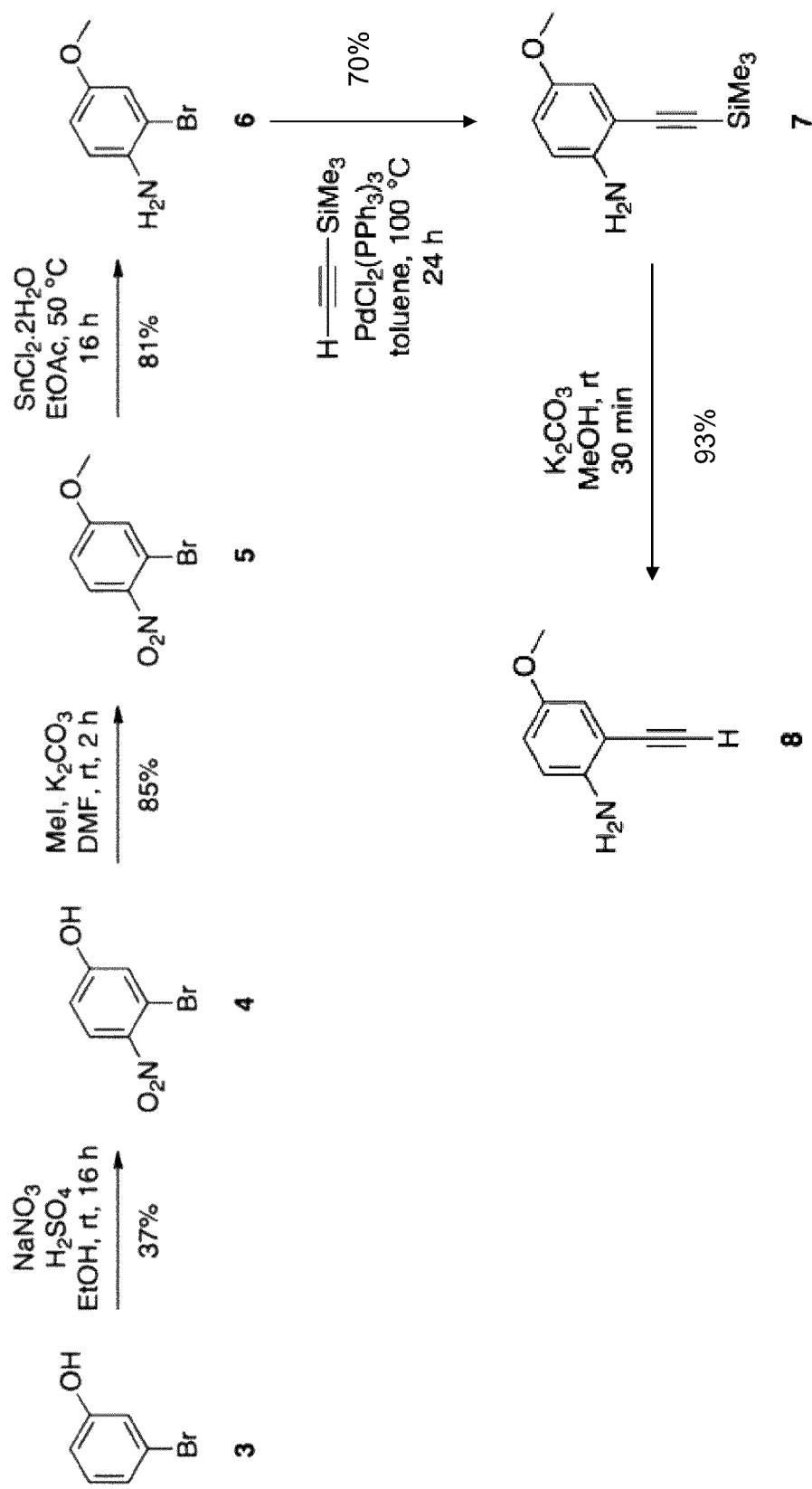
FIGS. 1A and 1B illustrate a synthesis of the compound of Formula 2.

The present invention generally relates to a small-molecule scaffold that substantially replicates the spatial and angular projections of several side chains on both faces of an α-helix, specifically the i and i+7 side chains on one face, and the i and i+2 side chains on the other. The small-molecule scaffold described herein allows for mimicry of a fifth amino acid side chain, allowing for even stronger binding interactions with its target protein. As a result of the binding interactions, the amphipathic α-helix mimetic can be used to disrupt disease-promoting protein-protein interactions that are mediated by α-helices, for example, Bak-Bcl-$x_L$, Bim-Mcl-1, c-Myc-Max, c-Jun-Fos, p53-HDM2, and the like.

It is known in the art that the rotation about the central axis of 1,2-diphenylacetylenes can be biased through the formation of an intramolecular hydrogen bond [20]. Furthermore, 1,2-diphenylacetylenes constrained in this way have been proposed as potential β-strand mimetics [21]. Motivated by an interest in mimicking amphipathic BH3 α-helices that engage the oncoproteins Bcl-$x_L$ and Mcl-1 [22], the present inventor surprisingly discovered that the 1,2-diphenylacetylene framework incorporating a similar intramolecular hydrogen bond could function as a scaffold suitable to elicit mimicry of both faces of an α-helix. Towards this goal, the present inventor designed the compounds of formulas 1a-1c in which the $R^1$-$R^5$ groups are intended to mimic the i and i+7 side chains on one face of an α-helix, and the i+2 and i+5 side chains on the other, as well as a fifth amino acid side chain for even stronger binding interactions with a target protein.

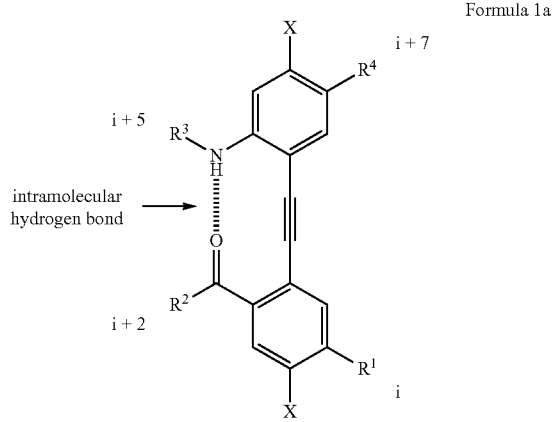

Formula 1a

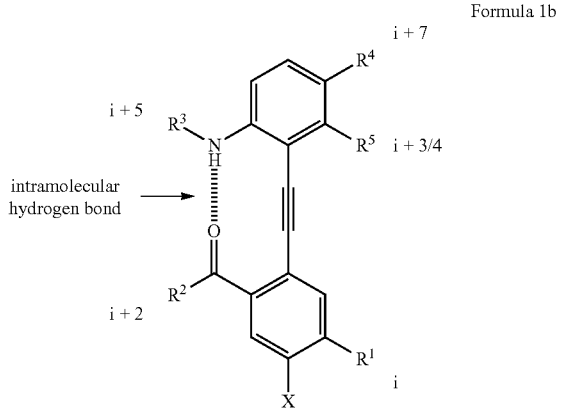

Formula 1b

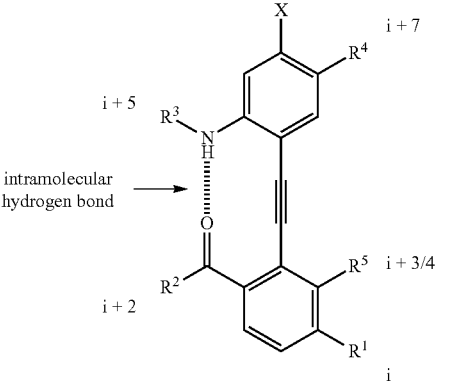

Formula 1c wherein:
$R^1$, $R^4$, $R^5$ can be alkyl, cycloalkyl, alkenyl, alkynyl, aryl, $CH_2$-aryl, heteroaryl, $CH_2$-heteroaryl, $CH_2CO_2H$, $CH_2CH_2CO_2H$, $CH_2OH$, $(CH_2)_4NH_2$, $(CH_2)_3N=C(NH_2)_2$, O-alkyl, O-cycloalkyl, O-alkenyl, O-alkynyl, O-aryl, O—$CH_2$-aryl, O-heteroaryl, O—$CH_2$-heteroaryl, O—$CH_2CO_2H$, O—$CH_2CH_2CO_2H$, O—$(CH_2)_2OH$, O—$(CH_2)_4NH_2$, O—$(CH_2)_3N=C(NH_2)_2$;

$R^2$ can be alkyl, cycloalkyl, alkenyl, alkynyl, aryl, $CH_2$-aryl, heteroaryl, $CH_2$-heteroaryl, O-alkyl, O-cycloalkyl, O-alkenyl, O-alkynyl, O-aryl, O—$CH_2$-aryl, O-heteroaryl, O—$CH_2$-heteroaryl, NH-alkyl, NH-cycloalkyl, NH-alkenyl, NH-alkynyl, NH-aryl, NH—$CH_2$-aryl, NH-heteroaryl, NH—$CH_2$-heteroaryl, CO-alkyl, CO-cycloalkyl, CO-alkenyl, CO-alkynyl, CO-aryl, CO—$CH_2$-aryl, CO-heteroaryl, CO—$CH_2$-heteroaryl, $CO_2$-alkyl, $CO_2$-cycloalkyl, $CO_2$-alkenyl, $CO_2$-alkynyl, $CO_2$-aryl, $CO_2$—$CH_2$-aryl, $CO_2$-heteroaryl, $CO_2$—$CH_2$-heteroaryl;

$R^3$ can be alkyl, cycloalkyl, alkenyl, alkynyl, aryl, $CH_2$-aryl, heteroaryl, $CH_2$-heteroaryl, CO-alkyl, CO-cycloalkyl, CO-alkenyl, CO-alkynyl, CO-aryl, CO—$CH_2$-aryl, CO-heteroaryl, CO—$CH_2$-heteroaryl, $CO_2$-alkyl, $CO_2$-cycloalkyl, $CO_2$-alkenyl, $CO_2$-alkynyl, $CO_2$-aryl, $CO_2$—$CH_2$-aryl, $CO_2$-heteroaryl, $CO_2$—$CH_2$-heteroaryl, $COCO_2H$, $COCO_2$-alkyl, $COCO_2$-cycloalkyl, $COCO_2$-alkenyl, $COCO_2$-alkynyl, $COCO_2$-aryl, $COCO_2$—$CH_2$-aryl, $COCO_2$-heteroaryl, $COCO_2$—$CH_2$-heteroaryl, $SO_2$-alkyl, $SO_2$-cycloalkyl, $SO_2$-alkenyl, $SO_2$-alkynyl, $SO_2$-aryl, $SO_2$—$CH_2$-aryl, $SO_2$-heteroaryl, $SO_2$—$CH_2$-heteroaryl; and X=H, $OCH_2CO_2H$, wherein the latter functions as a solubilizing group.

wherein any of the recited "alkyl," "cycloalkyl," "alkenyl," or "alkynyl" groups comprise one to eight carbon atoms, branched or unbranched, and wherein the recited "aryl" or "heteroaryl" groups comprise two to ten carbon atoms, substituted or unsubstituted, as readily understood by the person skilled in the art.

In one example, the compound is that of formula 1a wherein $R^1$ and $R^4$ are the same as or different from one another and are selected from the group consisting of O-alkyl, O-cycloalkyl, O-alkenyl, O-alkynyl, O-aryl, O—$CH_2$-aryl, O-heteroaryl, O—$CH_2$-heteroaryl, O—$CH_2CO_2H$, O—$CH_2CH_2CO_2H$, O—$(CH_2)_2OH$, O—$(CH_2)_4NH_2$, and O—$(CH_2)_3N=C(NH_2)_2$, $R^2$ is selected from the group consisting of NH-alkyl, NH-cycloalkyl, NH-alkenyl, NH-alkynyl, NH-aryl, NH—$CH_2$-aryl, NH-heteroaryl, and NH—$CH_2$-heteroaryl, $R^3$ is selected from the group consisting of CO-alkyl, CO-cycloalkyl, CO-alkenyl, CO-alkynyl, CO-aryl, CO—CH$_2$-aryl, CO-heteroaryl, CO—CH$_2$-heteroaryl, CO$_2$-alkyl, CO$_2$-cycloalkyl, CO$_2$-alkenyl, CO$_2$-alkynyl, CO$_2$-aryl, CO$_2$—CH$_2$-aryl, CO$_2$-heteroaryl, and CO$_2$—CH$_2$-heteroaryl, and X is H.

For example, the amphipathic α-helix mimetic comprises a compound of formula 2 or a compound of formula 14: (

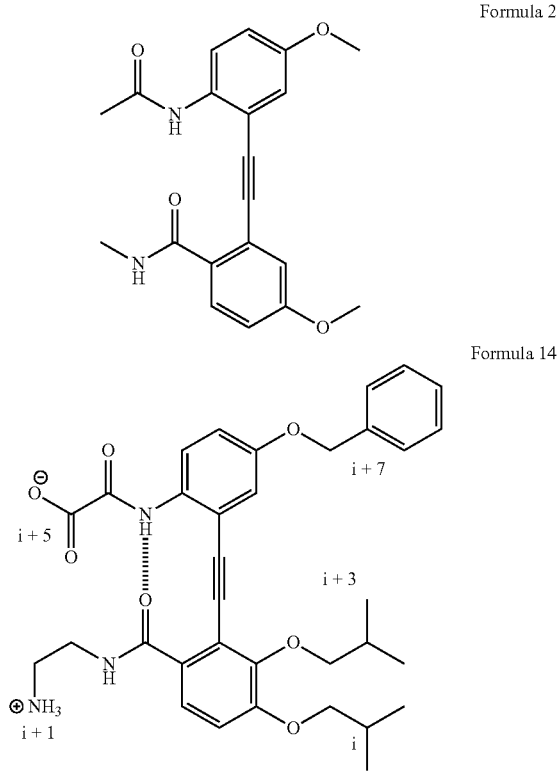

Formula 2

Formula 14

The desired structural integrity of the compounds of formulas 1a-1c is maintained by an intramolecular hydrogen bond between the NH of the amide in the upper subunit and the CO of the amide in the lower subunit [20]. Preferably, there is no rigid hydrogen bond, since the i, i+7 and the i+2, i+5 side chains of an α-helix are staggered, not eclipsed.

Figure 1B:
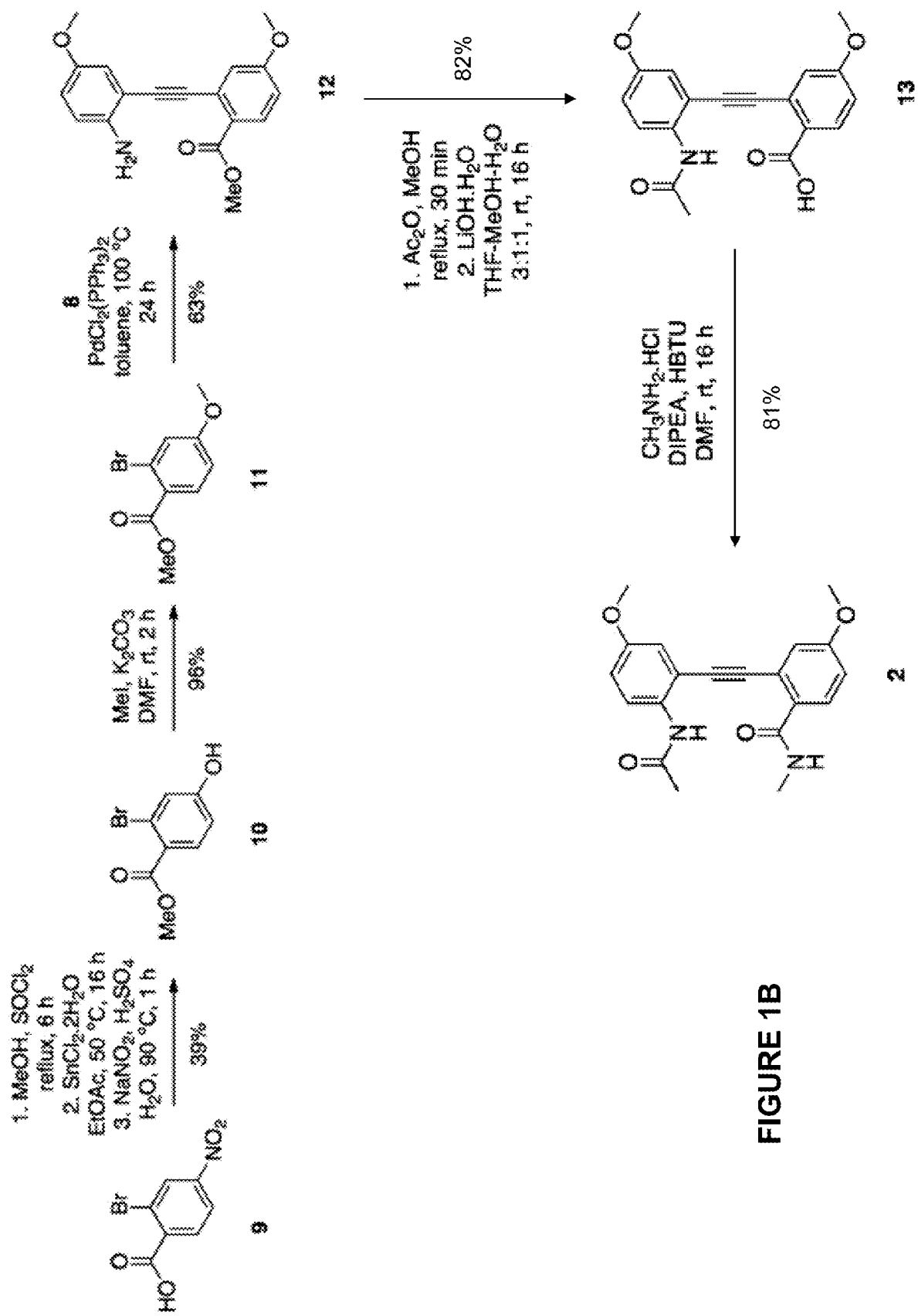

The synthesis of the compound of formula 2, a derivative of formula 1a where $R^1=R^4=$—O—CH$_3$, $R^3=$—C(O)CH$_3$, $R^2=$—NH—CH$_3$ and X=H, is illustrated in FIGS. 1A and 1B. Briefly, selective nitration of 3-bromophenol (3) gave 3-bromo-4-nitrophenol (4), which was subsequently O-methylated to yield 5, and then reduction of the nitro group with tin (II) chloride afforded aniline 6. In a key step in the synthesis of the compound of formula 2, a Sonogashira cross-coupling reaction of 6 with trimethylsilylacetylene delivered 7, which was then primed for a subsequent Sonogashira reaction by removal of the TMS group with potassium carbonate in MeOH to yield 8. Meanwhile, the carboxylic acid of 2-bromo-4-nitrobenzoic acid (9) was esterified, then the nitro group was chemoselectively reduced, diazotized and finally quenched with water to deliver methyl 2-bromo-4-hydroxybenzoate (10). After methylation of the hydroxyl group of 10, a second Sonogashira reaction between 8 and 11 furnished 1,2-diphenylacetylene 12. Acetylation, saponification and then coupling of the liberated carboxylic acid to methylamine gave the target molecule 2. Overall, the compound of formula 2 was accessed in an efficient, 13-step synthesis, in which most of the side chains (here, methyl groups) were introduced in the last few stages of the synthesis, which will directly facilitate the generation of compound libraries.

Figure 2:
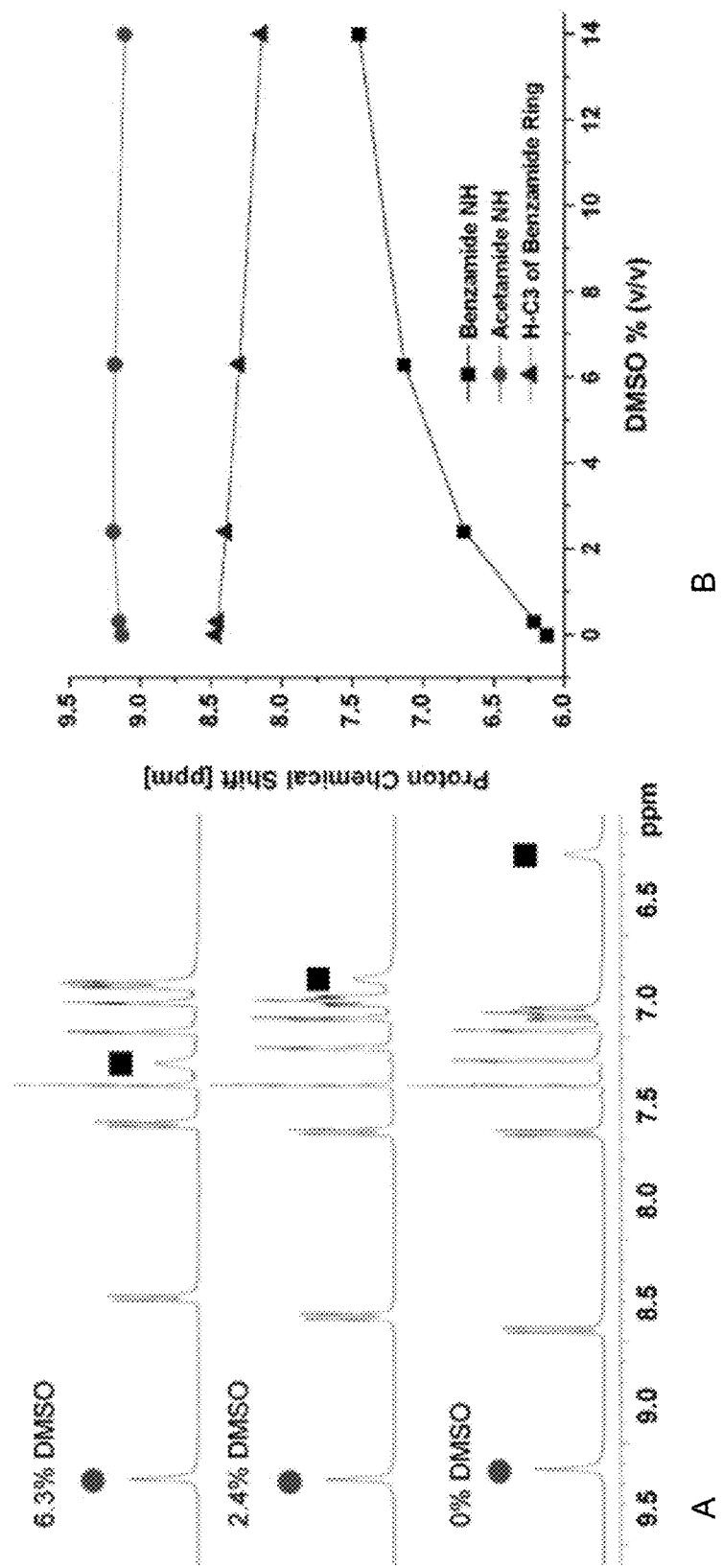
FIG. 2A illustrates the 1D ¹H NMR (400 MHz) spectra for the DMSO titration of the compound of formula 2 in $CDCl_3$ at 300K.
FIG. 2B illustrates the chemical shift vs [DMSO] for the DMSO titration of the compound of formula 2 in $CDCl_3$ at 300K.

Evidence that the intramolecular hydrogen bond exists includes $^1$H NMR (400 MHz) titrations of the compound of formula 2 in CDCl$_3$, with d$_6$-DMSO. The results are shown in FIG. 2. Hydrogen bonding results in deshielding, and an increasingly downfield-shifted proton resonance is indicative of stronger hydrogen bonding [24]. The acetamide NH ($\delta_H$ 9.14 ppm) is significantly downfield of both the benzamide NH in the compound of formula 2 ($\delta_H$ 6.10 ppm) and the acetamide NH in the control compound N-(4-methoxy-2-((trimethylsilyl)ethynyl)phenyl)acetamide ($\delta_H$ 7.78 ppm), neither of which can engage in intramolecular hydrogen bonding. Unlike the benzamide NH, the acetamide NH in the compound of formula 2 is protected from exchange with residual water in the sample (sharper resonance). Furthermore, with increasing concentrations of d$_6$-DMSO, the benzamide NH resonance shifts downfield as a consequence of stronger hydrogen-bonding interactions with DMSO. On the other hand, negligible changes in the acetamide NH chemical shift were observed, suggesting DMSO cannot contend with the postulated intramolecular hydrogen bond. Other chemical shifts were largely unchanged. Collectively, these data confirm the existence of the intramolecular hydrogen bond.

In order to evaluate the most likely conformation of the compounds of formula 1 under conditions that reflect those encountered in biological systems, the compound of formula 2 was computationally analyzed using 50 ns molecular dynamics (MD) simulations in explicit water using the program CHARMM [25]. A CHARMM-compatible force field for the compound of formula 2 was constructed in the framework of the CHARMM General Force Fields (CGenFF) version 2b7 [26]. Atom types, charges and parameters were initially assigned using the CGenFF program [27] [28] and manually refined to improve analogy with existing CGenFF model compounds and standard CHARMM force field charge assignment rules. The phenylacetylenyl monomer was defined as a polymerizable CHARMM residue and the various side chains as patches (keyword "PRES" in the CHARMM Residue Topology File (rtf) format specification), thus providing basic building block for convenient generation of a variety of derivatives for present and future research. Solution phase calculations of the compound of formula 2 were performed by placing a minimized conformation of the solute in a pre-equilibrated cubic cell containing 2025 TIP3P water molecules and removing all water molecules with atoms within 2 Å from any solute atom. In the presence of periodic boundary conditions [29], the system was then partially minimized for 200 steepest decent steps in order to alleviate any bad contacts or other strong interactions. Finally, the system was gradually heated to 298.15K during a 20 ps MD simulation and then equilibrated for 100 ps; the edge length of the box after equilibration was about 39 Å in both cases. This equilibration was followed by a 50 ns production simulation during which snapshots were taken at 2 ps intervals, yielding 25000 snapshots on which analysis was performed. The particle mesh Ewald method [30] was used for the treatment of the Coulomb interactions with a real space cutoff of 12 Å, a 6$^{th}$ order cubic spline and a kappa value of 0.32. For the LJ interactions, a force-switching function [31] was applied over the range of 10-12 Å, and a long-range correction was used to account for LJ interactions beyond the cutoff distance [29]. A timestep of 2 fs was used in conjunction with the "Leapfrog" algorithm [32] to integrate the equations of motion. The SHAKE algorithm [33] was applied to constrain the length of covalent bonds to hydrogen atoms to their equilibrium values. The Nose-Hoover thermostat [34], [35] and the Langevin piston barostat [36] were used to generate the isothermal-isobaric ensemble (NPT) with continuous dynamics.

Figure 3:
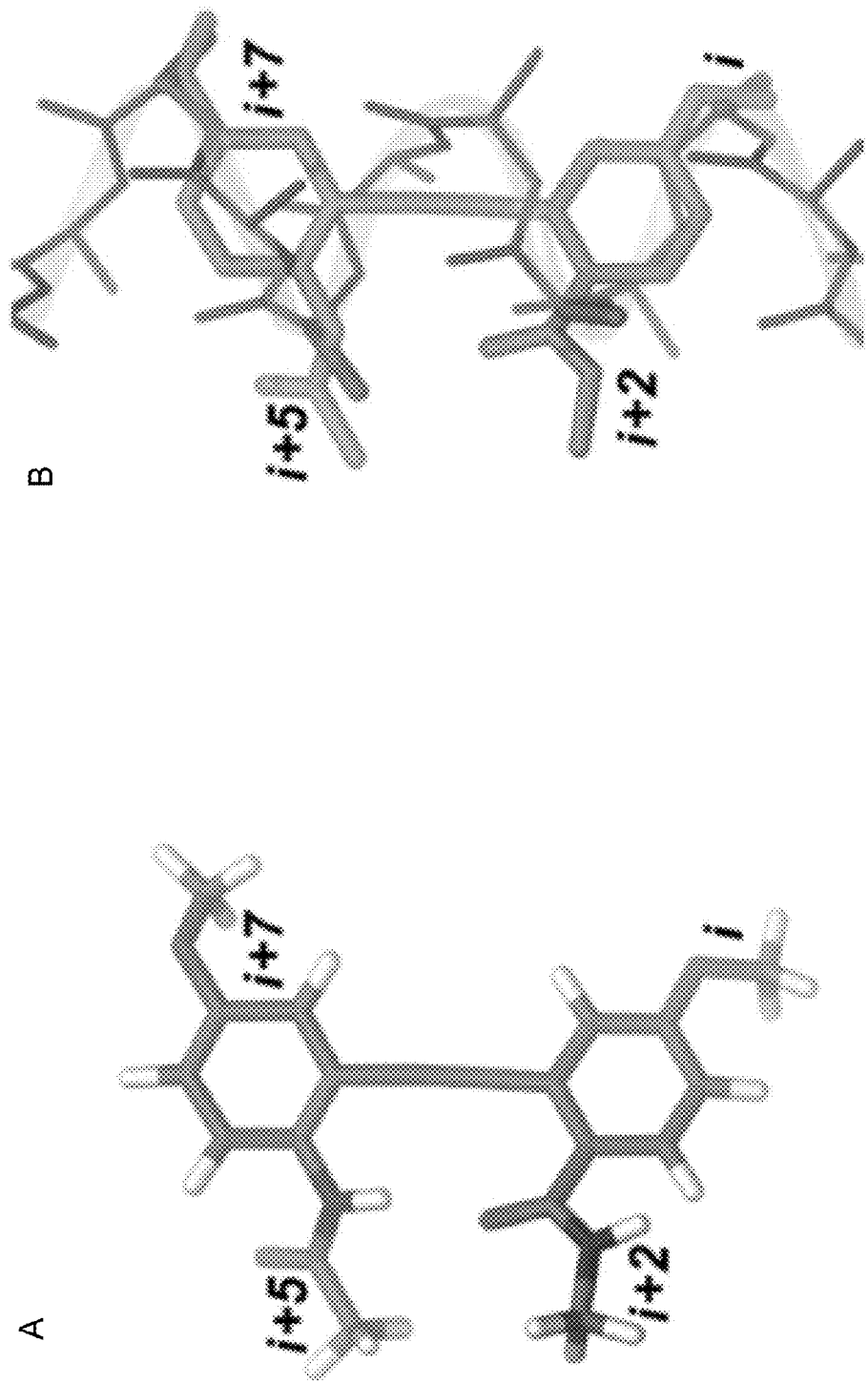
FIG. 3A illustrates the lowest-RMSD conformation of the compound of formula 2.
FIG. 3B illustrates the superimposition of the compound of formula 2 (orange) on a poly-alanine α-helix (green), wherein the hydrogen atoms were omitted for clarity.

It was determined that the i and i+7 side chains in the compound of formula 2 project from the same face (and the i+2 and i+5 from the other) during 69% of the simulation time. Further, the results implied that the strength of the NH...O=C hydrogen bond is approximately 0.5 kcal/mol in water. Together, these results demonstrate that the intramolecular hydrogen bond biases the conformation in aqueous medium rather than locking it rigidly into place. A superposition of a representative snapshot (FIG. 3A) of the peak population of the compound of formula 2 on an idealized poly-alanine α-helix is shown in FIG. 3B (RMSD=0.52 Å), which demonstrates that the compound of formula 2 replicates the spatial and angular projections of the i, i+2, i+5 and i+7 side chains of a native α-helix well. Hence, the compound of formula 2 achieves double-sided α-helix mimicry and, depending on the nature of the side chains, may also be applied to the mimicry of an amphipathic α-helix. Additionally, the computational analysis suggested that there is a relative weakness of the hydrogen bond in aqueous medium, which probably allows access to such desirable conformations of the compound of formula 2.

It is known that one approach by which apoptosis is tightly regulated is through the antagonistic interaction of the pro-survival protein Mcl-1 on the Bcl-2 family members, such as Bim and Bak [22]. Key residues of the Bim BH3 α-helix that engage Mcl-1 are Leu62 (i), Ile65 (i+3) and Phe69 (i+7) on one face of the helix, and Arg63 (i+1) and Asp67 (i+5) on the opposing face [37]. To determine if the compound of formulas 1a-1c could be elaborated to afford structural mimicry of an additional fifth residue, the present inventor designed amphipathic α-helix mimetic 14.

On the hydrophobic face of the compound of formula 14, the isobutyl groups were intended as mimetics of the side chains of Leu62 and Ile65, while the benzyl group was intended to mimic the side chain of Phe69. On the opposing face, a carboxylic acid reproduces the side chain of Asp67. It has been established that the N-methyl of the benzamide moiety of the compound of formula 2 is a good mimetic of the i+2 side chain. As such, the present inventor considered that this position might also reasonably mimic the i+1 side chain, particularly in the case of amino acids with flexible side chains, such as arginine and lysine. Therefore, on the polar face of 14, mimicry of Arg63 is proposed by a basic ethylamine moiety attached to the benzamide nitrogen.

Figure 4A:
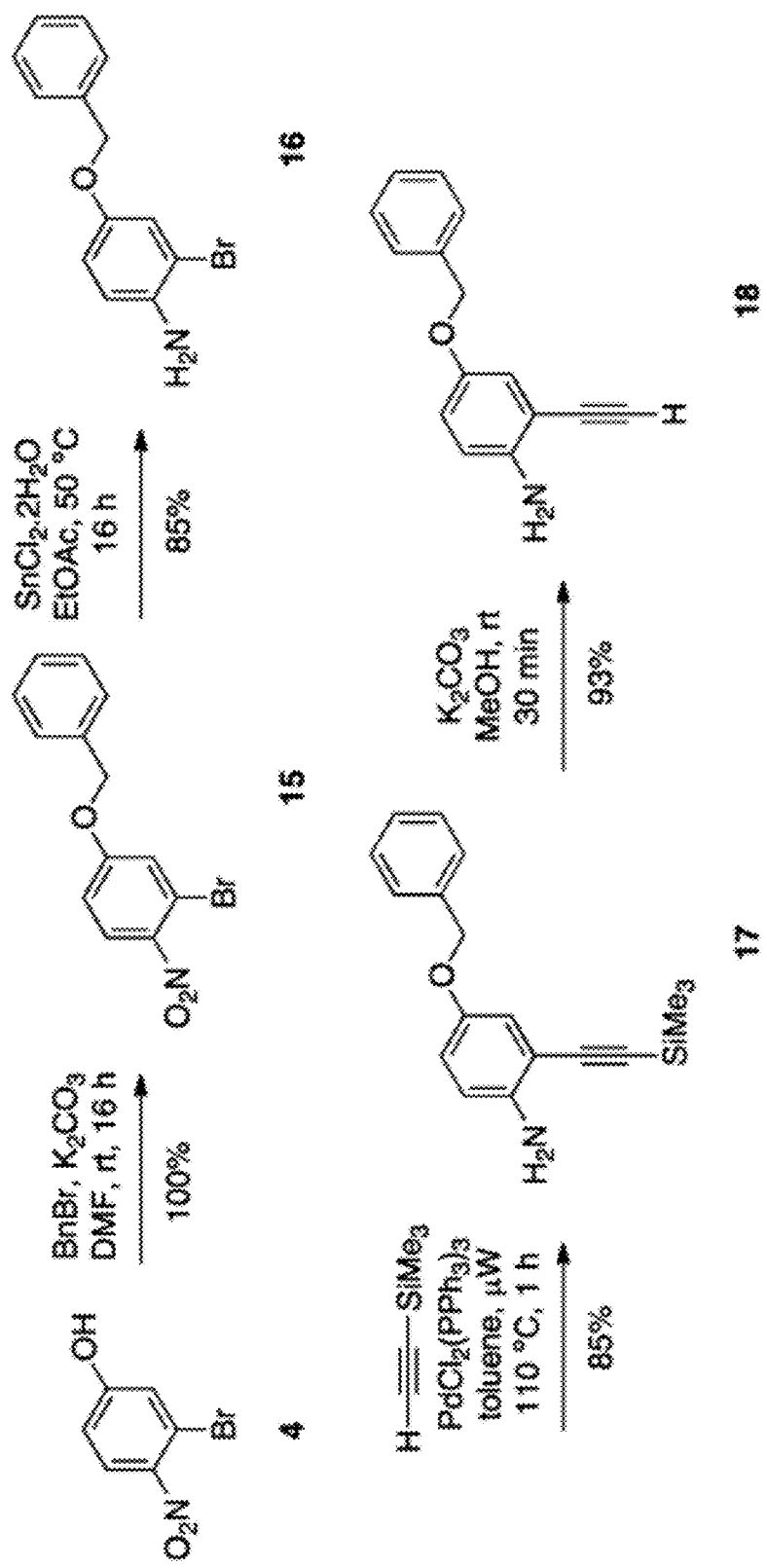
FIGS. 4A and 4B illustrate a synthesis of the compound of Formula 14.
Figure 4B:
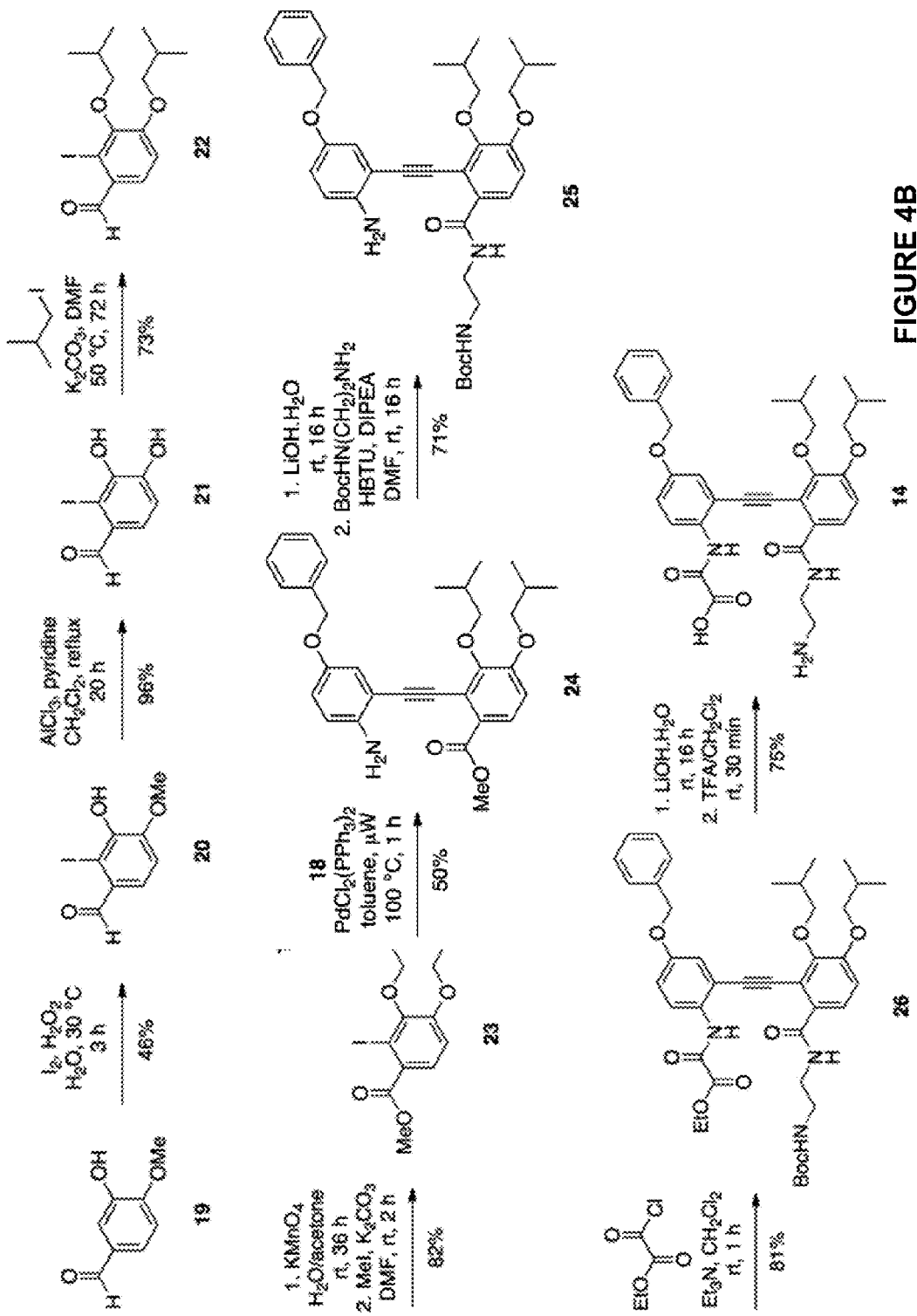
Figure 5:
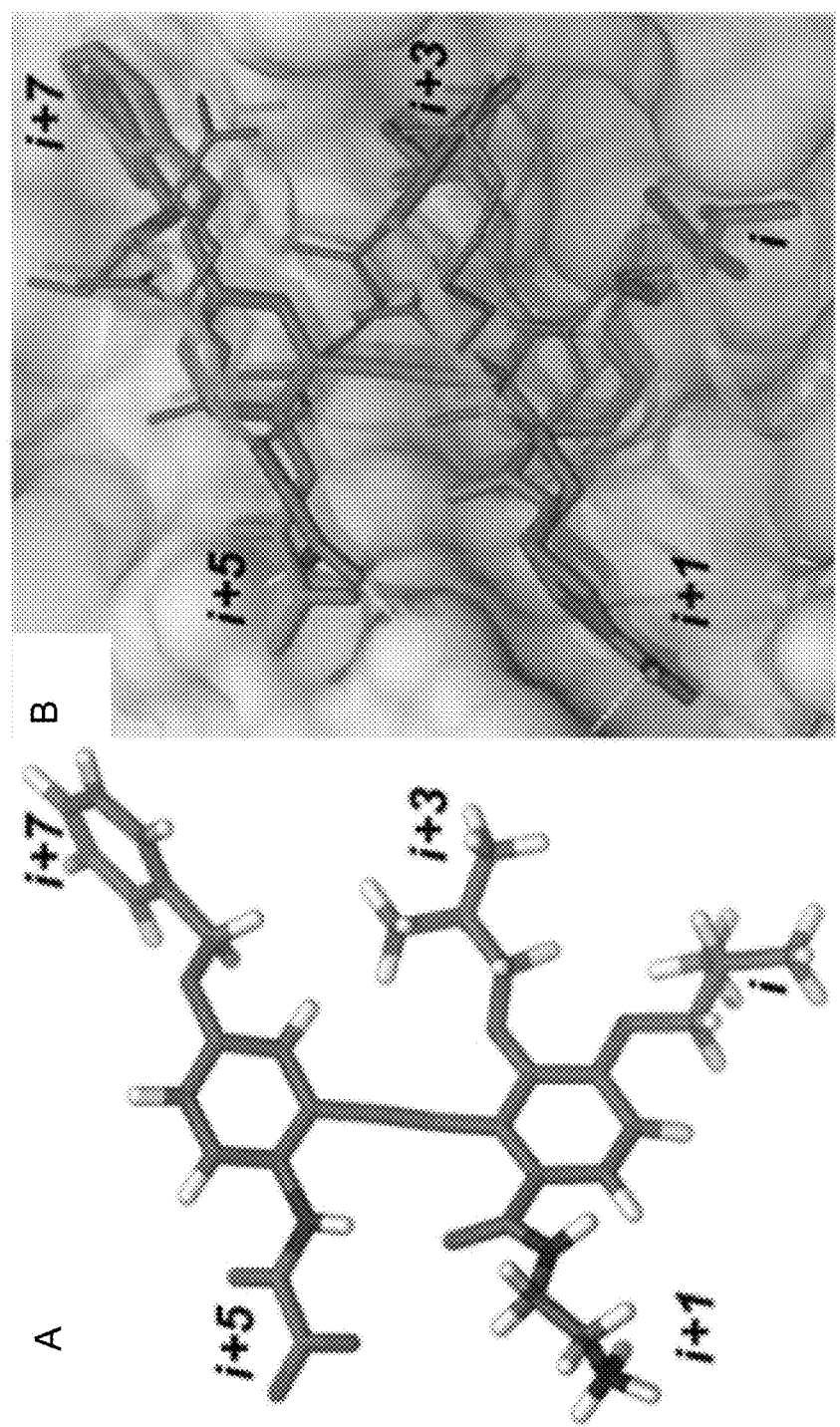
FIG. 5A illustrates the lowest-RMSD conformation of the compound of formula 14.
FIG. 5B illustrates the superimposition of the compound of formula 14 (orange) on the Bim BH3 α-helix (green), wherein the hydrogen atoms were omitted for clarity.

The synthesis of the compound of formula 14, a derivative of formula 1c where $R^1=R^5=$—O—CH$_2$—CH(CH$_3$)$_2$, $R^3=$—C(O)COOH, $R^2=$—NH—CH$_2$CH$_2$NH$_2$, $R^4=$—O—CH$_2$—C$_6$H$_6$, and X=H, is illustrated in FIGS. 4A and 4B. For the most part, the chemistry involved is similar to that for the synthesis of the compound of formula 2, with the greatest difference being the requirement to synthesize the more reactive iodoarene 24 to compensate for the increased steric hindrance in the Sonagashira cross-coupling reaction. As before, a 200 ns MD simulation in explicit water was used to determine the conformational preference of the compound of formula 14 under aqueous conditions. Here, the i and i+7 side chains project from the same face 83% of the time. The greater preference for the desired syn conformation relative to the compound of formula 2 is apparently due to a transient salt bridge. Superposition of a representative snapshot (FIG. 5A) of the peak population of the compound of formula 14 on the corresponding side chains in an x-ray structure [38] of the Bim-BH3 helix in complex with Mcl-1 (FIG. 5B, RMSD=1.91 Å), reveals excellent mimicry of the five key residues of the Bim-BH3 helix. Preliminary studies indicate that the compound of formula 14 antagonizes the Mcl-1-Bak-BH3 complex with an IC$_{50}$ of 3.24±0.48 μM.

Accordingly, in another aspect, a method of preparing the compound of formula 2 or a compound of formula 14 is described, for example as shown in FIGS. 1A and 1B and FIGS. 4A and 4B, respectively.

In still another aspect, a method of disrupting disease-promoting protein-protein interactions that are mediated by α-helices is disclosed, said method comprising interacting a compound of formulas 1a-1c with a protein such that the protein-protein interactions are antagonized and the disease promotion is disrupted, wherein the disease-promoting protein-protein interactions are selected from the group consisting of Bim-Mcl-1, c-Myc-Max, c-Jun-Fos, and p53-HDM2.

In one example, the method of disrupting disease-promoting protein-protein interactions that are mediated by α-helices comprises interacting a compound of formula 2 with a protein such that the protein-protein interactions are antagonized and the disease promotion is disrupted, wherein the disease-promoting protein-protein interactions are selected from the group consisting of Bim-Mcl-1, c-Myc-Max, c-Jun-Fos, and p53-HDM2.

In another example, a method of disrupting disease-promoting protein-protein interactions that are mediated by α-helices comprises interacting a compound of formula 14 with a protein such that the protein-protein interactions are antagonized and the disease promotion is disrupted, wherein the disease-promoting protein-protein interactions are selected from the group consisting of Bim-Mcl-1, c-Myc-Max, c-Jun-Fos, and p53-HDM2.

In another aspect, a pharmaceutical composition is described, said composition comprising a compound of formulas 1a-1c and a pharmaceutically acceptable excipient. Most preferably, the pharmaceutical composition comprises a compound of formula 2 or a compound of formula 14. Pharmaceutically acceptable excipients are understood to the person skilled in the art.

In summary, the present inventor has designed a 1,2-diphenylacetylene scaffold that projects functional groups at the correct spatial and angular geometries to substantially mimic the i, i+7 and i+2, i+5 side chains on opposite faces of an α-helix, and, therefore, allows for amphipathic α-helix mimicry. The synthesis is convergent and efficient, and the introduction of side chain chemical diversity is reserved until later stages in the synthesis, which facilitates the development of compound libraries. More superior α-helix mimicry was achieved by introducing additional functionality into the "lower" phenyl ring of the 1,2-diphenylacetylene scaffold, allowing for mimicry of the i+3 side chain in addition to i, i+1, i+5 and i+7 side chains. Advantageously, the non-peptidic, amphipathic α-helix mimetic can emulate up to five amino acid side chains located across both faces and within two complete turns of the helix.

EXAMPLES

Unless otherwise stated, all reactions were performed under an inert (N$_2$) atmosphere. Reagents and solvents were reagent grade and purchased from Sigma-Aldrich, Alfa Aesar, Oakwood and TCI America. $^1$H and $^{13}$C NMR spectra were recorded on a Varian INOVA 400 MHz NMR spectrometer at 25° C. Chemical shifts are reported in parts per million (ppm). Data for $^1$H NMR are reported as follows: chemical shift (δ ppm) (integration, multiplicity, coupling constant (Hz)). Multiplicities are reported as follows: s=singlet, d=doublet, t=triplet, q=quartet, sep=septet, dd=doublet of doublets, m=multiplet. Data for $^{13}$C are reported in terms of chemical shifts (δ ppm). The residual solvent peak was used as an internal reference. The mass spectra were obtained on an Electrospray TOF (ESI-TOF) mass spectrometer (Brukera-maZon X). Microwave assisted reactions were performed in a Biotage Initiator 2.5 microwave reactor.

Example 1

3-Bromo-4-nitrophenol (Compound 4)

Sulfuric acid (98%, 10.0 mL, 187.4 mmol) was added dropwise to a solution of NaNO$_3$ (13.5 g, 159.6 mmol) in H$_2$O (30 mL), keeping the temperature between 20 and 30° C. A solution of 3-bromophenol (12.0 g, 69.4 mmol) dissolved in EtOH (25 mL) was then added dropwise at this temperature. The reaction mixture was stirred at room temperature overnight, then poured into ice-water (300 mL), and extracted with dichloromethane (3×100 mL). The combined organic layer was dried over anhydrous Na$_2$SO$_4$, filtered, concentrated and purified by silica column chromatography (30% EtOAc in hexanes) to afford compound 4 in 37.1% (5.59 g) yield as a yellow solid. $^1$H-NMR (DMSO-d$_6$, 400 MHz) δ 11.2 (1H, s, OH), 7.98 (1H, d, J=8.4 Hz, Ar), 7.16 (1H, d, J=1.6 Hz, Ar), 6.90 (1H, dd, J=8.4 Hz, 1.6 Hz, Ar); $^{13}$C-NMR (CDCl$_3$, 100 MHz) δ 162.5, 141.0, 129.0, 121.4, 116.2, 115.7; MS (ESI) m/z Calcd for C$_6$H$_4$BrNO$_3$ (M$^+$): 216.9, Found: 217.9 (M+H$^+$).

Example 2

2-Bromo-4-methoxy-1-nitrobenzene (Compound 5)

Compound 4 (2.0 g, 9.22 mmol) was dissolved in DMF (40 mL), and K$_2$CO$_3$ (2.5 g, 18.44 mmol) was added. The reaction mixture was stirred at room temperature for 20 min. After cooling to 0° C., a solution of iodomethane (861 µL, 13.83 mmol) in DMF (5 mL) was added dropwise, and the resulting mixture was stirred at room temperature for 2 h. The reaction was quenched by adding H$_2$O (100 mL) and partitioned with Et$_2$O (200 mL). The organic layer was washed with H$_2$O (3×50 mL) and brine (50 mL). The organic layer was collected, dried over anhydrous Na$_2$SO$_4$, filtered, concentrated, and purified by silica column chromatography (20% EtOAc in hexanes) to afford compound 5 in 85.0% (1.81 g) yield as a yellow solid. $^1$H-NMR (CDCl$_3$, 400 MHz) δ 7.89 (1H, d, J=9.2 Hz, Ar), 7.22 (1H, s, Ar), 6.91 (1H, d, J=9.2 Hz, Ar), 3.89 (3H, s, OCH$_3$); MS (ESI) m/z Calcd for C$_7$H$_6$BrNO$_3$ (M$^+$): 231.0, Found: 232.1 (M+H$^+$).

Example 3

2-Bromo-4-methoxyaniline (Compound 6)

Compound 5 (2.0 g, 8.75 mmol) was dissolved in EtOAc (87 mL). SnCl$_2$.2H$_2$O (9.9 g, 43.75 mmol) was added, then the reaction mixture was stirred at 50° C. overnight. The reaction mixture was diluted with EtOAc (400 mL), and partitioned with sat'd NaHCO$_3$(aq). The organic layer was collected, dried over anhydrous Na$_2$SO$_4$, filtered, concentrated, and purified by silica column chromatography (33% EtOAc in hexanes) to afford compound 6 in 80.7% (1.42 g) yield as a brown oil. $^1$H-NMR (CDCl$_3$, 400 MHz) δ 7.00 (1H, s, Ar), 6.72 (2H, m, Ar), 3.82 (2H, m, NH$_2$), 3.73 (3H, s, OCH$_3$); $^{13}$C-NMR (CDCl$_3$, 100 MHz) δ 152.6, 137.9, 117.5, 116.6, 115.0, 109.6, 55.9; MS (ESI) m/z Calcd for C$_7$H$_8$BrNO (M$^+$): 201.0, Found: 202.0 (M+H$^+$).

Example 4

4-Methoxy-2-((trimethylsilyl)ethynyl)aniline (Compound 7)

Compound 6 (1.40 g, 6.97 mmol), triphenylphosphine (55 mg, 3 mol %) and copper (I) iodide (13 mg, 1 mol %) were added to an oven-dried reaction flask containing toluene (27 mL) and Et$_3$N (7 mL). The reaction mixture was stirred at room temperature for 5 min with N$_2$ (g) bubbling. Bis(triphenylphosphine)palladium (II) dichloride (48 mg, 1 mol %) and a solution of trimethylsilylacetylene (1.49 mL, 10.46 mmol) in Et$_3$N (3 mL) were added. The reaction mixture was stirred at 100° C. for 24 h. The reaction was cooled to room temperature, then diluted with EtOAc (300 mL) and washed with brine (3×70 mL). The organic layer was collected, dried over anhydrous Na$_2$SO$_4$, filtered, concentrated and purified by silica column chromatography (8% EtOAc in hexanes) to afford compound 7 in 70.0% (1.07 g) yield as a brown oil. $^1$H-NMR (CDCl$_3$, 400 MHz) δ 6.81 (1H, s, Ar), 6.74 (1H, d, J=8.8 Hz, Ar), 6.63 (1H, d, J=8.8 Hz, Ar), 3.70 (3H, s, OCH$_3$), 3.50 (2H, bs, NH$_2$), 0.24 (9H, s, Si(CH$_3$)$_3$); $^{13}$C-NMR (CDCl$_3$, 100 MHz) δ 151.7, 142.4, 117.7, 115.8, 115.6, 108.3, 101.7, 99.7, 55.7, 0.08; MS (ESI) m/z Calcd for C$_{12}$H$_{17}$NOSi (M$^+$): 219.1, Found: 220.1 (M+H$^+$).

Example 5

2-Ethynyl-4-methoxyaniline (Compound 8)

Compound 7 (1.07 g, 4.88 mmol) was dissolved in MeOH (40 mL). K$_2$CO$_3$ (1.35 g, 9.77 mmol) was added, and then the reaction mixture was stirred at room temperature for 30 min. After evaporation of most of the solvent, the crude material was diluted in EtOAc (200 mL), and washed with H$_2$O (2×50 mL) and brine (50 mL). The organic layer was collected, dried over anhydrous Na$_2$SO$_4$, filtered, concentrated and purified by silica column chromatography (20% EtOAc in hexanes) to afford compound 8 in 93.0% (667 mg) yield as a dark brown oil. $^1$H-NMR (CDCl$_3$, 400 MHz) δ 6.87 (1H, d, J=2.4 Hz, Ar), 6.79 (1H, dd, J=8.4 Hz, 2.4 Hz, Ar), 6.64 (1H, d, J=8.4 Hz, Ar), 3.97 (2H, bs, NH$_2$), 3.73 (3H, s, OCH$_3$), 3.38 (1H, s, CH); $^{13}$C-NMR (CDCl$_3$, 100 MHz) δ 151.7, 142.7, 117.8, 116.2, 115.9, 107.2, 82.3, 80.6, 55.7; MS (ESI) m/z Calcd for C$_9$H$_9$NO (M$^+$): 147.1, Found: 148.0 (M+H$^+$).

Example 6

Methyl 2-bromo-4-hydroxybenzoate (10)

2-Bromo-4-nitrobenzoic acid (6.2 g, 25.3 mmol) was dissolved in MeOH (120 mL), and SOCl$_2$ (5.5 mL, 75.9 mmol) was added dropwise at 0° C. The reaction mixture was refluxed for 6 h. The reaction solvent was concentrated to dryness. Residual SOCl$_2$ was removed by co-evaporation with CH$_2$Cl$_2$ (×3). The solid was dried under vacuum to afford methyl 2-bromo-4-nitrobenzoate in 99.5% (6.52 g) yield as a light yellow solid. $^1$H-NMR (CDCl$_3$, 400 MHz) δ 8.50 (1H, s, Ar), 8.21 (1H, d, J=8.4 Hz, Ar), 7.91 (1H, d, J=8.4 Hz, Ar), 3.97 (3H, s, OCH$_3$); $^{13}$C-NMR (CDCl$_3$, 100 MHz) δ 165.2, 149.2, 137.9, 131.7, 129.1, 122.1, 122.0, 53.1; MS (ESI) m/z Calcd for C$_8$H$_6$BrNO$_4$ (M$^+$): 259.0, Found: 260.1 (M+H$^+$). Next, the nitro group of methyl 2-bromo-4-nitrobenzoate (6.38 g, 24.6 mmol) was chemoselectively reduced with 5 nCl$_2$.2H$_2$O (27.8 g, 123.2 mmol) in a manner similar to that described for compound 6 to deliver methyl 4-amino-2-bromobenzoate in 96.0% (5.41 g) yield as a yellow solid. $^1$H-NMR (CDCl$_3$, 400 MHz) δ 7.74 (1H, d, J=8.8 Hz, Ar), 6.90 (1H, d, J=1.6 Hz, Ar), 6.55 (1H, dd, J=8.8 Hz, 1.6 Hz, Ar), 4.06 (2H, s, NH$_2$), 3.83 (3H, s, OCH$_3$); $^{13}$C-NMR (CDCl$_3$, 100 MHz) δ 165.9, 150.4, 133.6, 124.1, 119.7, 119.6, 112.7, 51.8; MS (ESI) m/z Calcd for C$_8$H$_8$BrNO$_2$ (M$^+$): 229.0, Found: 230.1 (M+H$^+$). Finally, a solution of sulfuric acid (98%, 6 mL) in H$_2$O (75 mL) was added to methyl 4-amino-2-bromobenzoate (1.23 g, 5.38 mmol) and the resulting suspension was heated to 90° C., then stirred for 5 h at this temperature. The reaction mixture was cooled to 0° C. and a solution of NaNO$_2$ (384 mg, 5.57 mmol) in H$_2$O (5 mL) was added dropwise, then the reaction was allowed to warm to ambient temperature. The reaction mixture was then added to a solution of sulfuric acid (98%, 6 mL) in H$_2$O (75 mL) that had been preheated to 90° C. The reaction mixture was stirred at 90° C. for 1 h, and then allowed to cool. The reaction mixture was partitioned between EtOAc (200 mL) and aqueous solution. The organic layer was collected, dried over anhydrous Na$_2$SO$_4$, filtered, concentrated and purified by silica column chromatography (35% EtOAc in hexanes) to afford compound 10 in 41.1% (508 mg) yield as a light brown solid. $^1$H-NMR (CDCl$_3$, 400 MHz) δ 7.76 (1H, d, J=8.8 Hz, Ar), 7.09 (1H, s, Ar), 6.75 (1H, d, J=8.8 Hz, Ar), 3.84 (3H, s, OCH$_3$); $^{13}$C-NMR (CDCl$_3$, 100 MHz) δ 166.2, 160.3, 133.5, 123.4, 122.1, 121.4, 114.3, 52.1; MS (ESI) m/z Calcd for C$_8$H$_7$BrO$_3$ (M$^+$): 230.0, Found: 231.0 (M+H$^+$).

Example 7

Methyl 2-bromo-4-methoxybenzoate (Compound 11)

Compound 10 (815 mg, 3.54 mmol) was dissolved in DMF (20 mL). K$_2$CO$_3$ (1.17 g, 8.50 mmol) was added, then the reaction mixture was stirred at room temperature for 20 min. The reaction mixture was cooled to 0° C., a solution of iodomethane (265 µL, 4.25 mmol) in DMF (1 mL) was added dropwise, and then the reaction was stirred at room temperature for 2 h. The reaction was quenched by adding H$_2$O (50 mL), then partitioned with Et$_2$O (200 mL). The Et$_2$O layer was washed with H$_2$O (3×40 mL) and brine (40 mL). The organic layer was collected, dried over anhydrous Na$_2$SO$_4$, filtered, concentrated, and purified by silica column chromatography (15% EtOAc in hexanes) to afford compound 11 in 95.9% (849 mg) yield as a brown liquid. $^1$H-NMR (CDCl$_3$, 400 MHz) δ 7.87 (1H, d, J=8.4 Hz, Ar), 7.19 (1H, s, Ar), 6.88 (1H, d, J=8.4 Hz, Ar), 3.90 (3H, s, OCH$_3$), 3.84 (3H, s, OCH$_3$); $^{13}$C-NMR (CDCl$_3$, 100 MHz) δ 165.8, 162.2, 133.1, 123.5, 123.3, 119.7, 113.0, 55.6, 52.1; MS (ESI) m/z Calcd for C$_9$H$_9$BrO$_3$ (M$^+$): 244.0, Found: 244.1 (M$^+$).

Example 8

Methyl 2-((2-amino-5-methoxyphenyl)ethynyl)-4-methoxybenzoate (Compound 12)

Compound 11 (106 mg, 0.43 mmol) and copper (I) iodide (1.6 mg, 2 mol %) were added to an oven-dried reaction flask containing toluene (2 mL) and Et$_3$N (2 mL). The reaction mixture was stirred at room temperature for 5 min with N$_2$ (g) bubbling. Bis(triphenylphosphine)palladium(II) dichloride (3 mg, 1 mol %) and a solution of compound 8 (63 mg, 0.43 mmol) in Et$_3$N (1 mL) were added. The reaction mixture was stirred at 100° C. for 24 h. The reaction was cooled to room temperature, then diluted with EtOAc (50 mL) and washed with brine (3×20 mL). The organic layer was collected, dried over anhydrous Na$_2$SO$_4$, filtered, concentrated and purified by silica column chromatography (20% EtOAc in hexanes) to afford compound 12 in 62.8% (84 mg) yield as a brown solid. $^1$H-NMR (CDCl$_3$, 400 MHz) δ 8.00 (1H, d, J=8.4 Hz, Ar), 7.14 (1H, s, Ar), 6.93 (1H, d, J=1.6 Hz, Ar), 6.88 (1H, dd, J=8.4 Hz, 1.6 Hz, Ar), 6.81 (1H, dd, J=8.4 Hz, 1.6 Hz, Ar), 6.68 (1H, d, J=8.4 Hz, Ar), 4.79 (2H, s, NH$_2$), 3.89 (6H, s, 2×OCH$_3$), 3.76 (3H, s, OCH$_3$); $^{13}$C-NMR (CDCl$_3$, 100 MHz) δ 165.9, 162.3, 151.4, 144.5, 132.8, 126.6, 122.9, 118.5, 117.9, 115.8, 115.6, 114.4, 107.6, 93.9, 92.6, 56.0, 55.7, 52.2; MS (ESI) m/z Calcd for C$_{18}$H$_{17}$NO$_4$ (M$^+$): 311.1, Found: 312.0 (M+H$^+$).

Example 9

2-((2-Acetamido-5-methoxyphenyl)ethynyl)-4-methoxybenzoic acid (Compound 13)

Compound 12 (84 mg, 0.27 mmol) was dissolved in MeOH (4 mL), and then acetic anhydride (28 µL, 0.30 mmol) was added. The reaction mixture was refluxed for 30 min. The reaction solvent was removed by evaporation, and then the residue was dissolved in CH$_2$Cl$_2$ (30 mL), and washed with H$_2$O (3×10 mL). The organic layer was collected, dried over Na$_2$SO$_4$, filtered, concentrated and purified by silica column chromatography (40% EtOAc in hexanes) to afford methyl 2-((2-acetamido-5-methoxyphenyl)ethynyl)-4-methoxybenzoate in 81.8% (78 mg) yield as a yellow solid. $^1$H-NMR (CDCl$_3$, 400 MHz) δ 9.30 (1H, s, NH), 8.51 (1H, d, J=9.6 Hz, Ar), 8.03 (1H, d, J=8.8 Hz, Ar), 7.14 (1H, s, Ar), 7.01 (1H, s, Ar), 6.93 (1H, d, J=9.6 Hz, Ar), 6.89 (1H, d, J=8.8 Hz, Ar), 3.88 (6H, s, 2×OCH$_3$), 3.79 (3H, s, OCH$_3$), 2.39 (3H, s, CH$_3$); $^{13}$C-NMR (CDCl$_3$, 100 MHz) δ 169.8, 166.0, 162.7, 154.9, 135.3, 132.8, 126.2, 122.5, 121.2, 118.2, 116.7, 116.2, 114.9, 112.4, 94.6, 91.0, 55.8, 55.7, 52.3, 24.6; MS (ESI) m/z Calcd for C$_{20}$H$_{19}$NO$_5$ (M$^+$): 353.1, Found: 352.0 (M−H$^+$). LiOH.H$_2$O (25 mg, 0.60 mmol) was added to a solution of methyl 2-((2-acetamido-5-methoxyphenyl)ethynyl)-4-methoxybenzoate (41 mg, 0.12 mmol) in THF/MeOH/H$_2$O (ratio=3:1:1, 2 mL). The reaction mixture was stirred at room temperature overnight. The reaction mixture was neutralized by adding 1M HCl (aq) and partitioned between EtOAc and sat'd NaH$_2$PO$_4$ (aq). The organic layer was collected, dried over Na$_2$SO$_4$, filtered, concentrated and dried under vacuum to afford compound 13 in 99.5% (40 mg) yield as a brown solid. $^1$H-NMR (DMSO-d$_6$, 400 MHz) δ 9.69 (1H, s, NH), 8.27 (1H, d, J=8.4 Hz, Ar), 8.01 (1H, d, J=8.0 Hz, Ar), 7.19 (1H, s, Ar), 7.08 (1H, s, Ar), 7.06 (1H, d, J=8.0 Hz, Ar), 6.99 (1H, d, J=8.4 Hz, Ar), 3.87 (3H, s, OCH$_3$), 3.77 (3H, s, OCH$_3$), 2.26 (3H, s, CH$_3$); $^{13}$C-NMR (DMSO-d$_6$, 100 MHz) δ 169.5, 167.6, 161.4, 154.8, 135.0, 133.1, 124.3, 121.6, 117.5, 116.6, 115.6, 115.2, 113.2, 96.1, 89.8, 56.0, 55.7, 24.5; MS (ESI) m/z Calcd for C$_{19}$H$_{17}$NO$_5$ (M$^+$): 339.1, Found: 338.1 (M−H$^+$).

Example 10

2-((2-Acetamido-5-methoxyphenyl)ethynyl)-4-methoxy-N-methylbenzamide (Compound 2)

To a solution of compound 13 (40 mg, 0.12 mmol), HBTU (68 mg, 0.18 mmol) and CH$_3$NH$_2$.HCl (12 mg, 0.18 mmol) in DMF (2 mL) was added DIPEA (84 µL, 0.48 mmol). The reaction mixture was stirred at room temperature overnight, then diluted with EtOAc (40 mL), and washed with H$_2$O (4×10 mL). The organic layer was collected, dried over $Na_2SO_4$, filtered, concentrated and purified by silica column chromatography (30% EtOAc in $CH_2Cl_2$) to afford compound 2 in 80.5% (34 mg) yield as a white solid. $^1$H-NMR ($CDCl_3$, 400 MHz) δ 9.15 (1H, s, NH), 8.47 (1H, d, J=8.8 Hz, Ar), 7.50 (1H, d, J=8.8 Hz, Ar), 7.13 (1H, s, Ar), 6.98 (1H, s, Ar), 6.92-6.87 (2H, m, Ar), 6.15 (1H, s, NH), 3.87 (3H, s, $OCH_3$), 3.79 (3H, s, $OCH_3$), 2.98 (3H, d, J=3.2 Hz, $CH_3$NH), 2.45 (3H, s, $CH_3$); $^{13}$C-NMR ($CDCl_3$+$CD_3OD$, 100 MHz) δ 170.5, 168.2, 160.8, 154.8, 134.4, 129.0, 128.6, 123.2, 121.5, 117.7, 116.0, 115.9, 114.6, 112.9, 93.8, 89.5, 55.4, 26.7, 24.0; MS (ESI) m/z Calcd for $C_{20}H_{20}N_2O_4$ ($M^+$): 352.1, Found: 352.1 ($M^+$).

Example 11

4-(Benzyloxy)-2-bromo-1-nitrobenzene (Compound 15)

Compound 4 (930 mg, 4.29 mmol) was dissolved in DMF (40 mL), then $K_2CO_3$ (890 mg, 6.44 mmol) was added. The reaction mixture was stirred at room temperature for 20 min, at which point benzyl bromide (407 μL, 3.43 mmol) was added. After stirring overnight at room temperature, the reaction was quenched by adding $H_2O$ (100 mL), and partitioned with $Et_2O$ (200 mL). The organic layer was washed with $H_2O$ (3×50 mL) and brine (50 mL). The organic layer was collected, dried over anhydrous $Na_2SO_4$, filtered, concentrated, and purified by silica column chromatography (15% EtOAc in hexanes) to afford compound 15 in 99.5% (1.05 g) yield as a brown solid. $^1$H-NMR ($CDCl_3$, 400 MHz) δ 7.99 (1H, d, J=8.4 Hz, Ar), 7.41 (5H, m, Ar), 7.31 (1H, s, Ar), 6.99 (1H, d, J=8.4 Hz, Ar), 5.13 (2H, s, $OCH_2$); $^{13}$C-NMR ($CDCl_3$, 100 MHz) δ 161.7, 142.5, 134.9, 128.8, 128.6, 127.9, 127.5, 121.0, 116.8, 114.1, 70.9; MS (ESI) m/z Calcd for $C_{13}H_{10}BrNO_3$ ($M^+$): 307.0, Found: 308.1 ($M+H^+$).

Example 12

4-(Benzyloxy)-2-bromoaniline (Compound 16)

The title compound 16 was prepared from compound 15 (1.06 g, 3.46 mmol) and 5 $nCl_2.2H_2O$ (3.90 g, 17.28 mmol) in a manner similar to that described for compound 6 in 72.2% (692 mg) yield as a brown solid. $^1$H-NMR ($CDCl_3$, 400 MHz) δ 7.40-7.33 (5H, m, Ar), 7.10 (1H, s, Ar), 6.81 (1H, d, J=8.0 Hz, Ar), 6.73 (1H, d, J=8.0 Hz, Ar), 4.97 (2H, s, $OCH_2$), 3.79 (2H, bs, $NH_2$); $^1$H-NMR ($CDCl_3$, 400 MHz) δ 151.8, 138.1, 136.9, 128.5, 127.9, 127.5, 118.9, 116.5, 116.0, 109.6, 70.9; MS (ESI) m/z Calcd for $C_{13}H_{12}BrNO$ ($M^+$): 227.0, Found: 228.1 ($M+H^+$).

Example 13

4-(Benzyloxy)-2-((trimethylsilyl)ethynyl)aniline (Compound 17)

Compound 16 (388 mg, 1.40 mmol), triphenylphosphine (37 mg, 10 mol %) and copper (I) iodide (53 mg, 10 mol %) were added to a 20 ml-oven-dried microwave vial containing toluene (3.0 mL) and $Et_3N$ (3.0 mL). The reaction mixture was stirred at room temperature for 5 min with $N_2$ (g) bubbling. Bis(triphenylphosphine)palladium(II) dichloride (98 mg, 10 mol %) and a solution of trimethylsilylacetylene (300 μL, 2.10 mmol) in $Et_3N$ (1.0 mL) were added successively. The reaction was placed in the microwave reactor and heated to 110° C. for 1 h. The reaction was cooled to room temperature and diluted with EtOAc (60 mL), and washed with brine (3×30 mL). The organic layer was collected, dried over anhydrous $Na_2SO_4$, filtered, concentrated and purified by silica column chromatography (30% EtOAc in hexanes) to afford compound 17 in 85.2% (352 mg) yield as a yellow oil. $^1$H-NMR ($CDCl_3$, 400 MHz) δ 7.38-7.29 (5H, m, Ar), 6.92 (1H, s, Ar), 6.81 (1H, d, J=8.8 Hz, Ar), 6.63 (1H, d, J=8.8 Hz, Ar), 4.95 (3H, s, $OCH_3$), 4.00 (2H, bs, $NH_2$), 0.24 (9H, s, Si($CH_3$)$_3$); $^{13}$C-NMR ($CDCl_3$, 100 MHz) δ 150.8, 142.7, 137.2, 128.4, 127.8, 127.4, 118.7, 117.2, 115.7, 108.3, 101.6, 99.8, 70.8, 0.09; MS (ESI) m/z Calcd for $C_{18}H_{21}NOSi$ ($M^+$): 295.1, Found: 296.1 ($M+H^+$).

Example 14

4-(Benzyloxy)-2-ethynylaniline (Compound 18)

The title compound 18 was prepared from compound 17 (177 mg, 0.60 mmol) and $K_2CO_3$ (166 mg, 1.20 mmol) in a manner similar to that described for compound 8 in 99.5% (133 mg) yield as a dark brown solid. $^1$H-NMR ($CDCl_3$, 400 MHz) δ 7.40-7.32 (5H, m, Ar), 6.96 (1H, s, Ar), 6.86 (1H, d, J=8.8 Hz, Ar), 6.66 (1H, d, J=8.8 Hz, Ar), 4.97 (2H, s, $OCH_2$), 3.99 (2H, s, $NH_2$), 3.37 (1H, s, CH); $^{13}$C-NMR ($CDCl_3$, 100 MHz) δ 150.8, 143.0, 137.1, 128.5, 127.8, 127.4, 118.8, 117.7, 115.8, 107.2, 82.4, 80.5, 70.5; MS (ESI) m/z Calcd for $C_{15}H_{13}NO$ ($M^+$): 223.1, Found: 224.0 ($M+H^+$).

Example 15

3-Hydroxy-2-iodo-4-methoxybenzaldehyde (Compound 20)

A mixture of 3-hydroxy-4-methoxybenzaldehyde (4.56 g, 30.0 mmol), pyridine (4.44 mL, 56.0 mmol) and iodine (3.82 g, 15.0 mmol) in $H_2O$ (200 mL) was maintained at 30° C. $H_2O_2$ (30%, 4.38 mL) was added over 1 h. Upon addition of all of the $H_2O_2$, the reaction mixture was stirred for a further 2 h, and then 10% aqueous $Na_2SO_3$ (45 mL) was added, maintaining the reaction temperature at 40° C. for 30 min. After another 1 h at room temperature, a yellow precipitate was detected, which was collected by filtration. The precipitate was washed with $H_2O$ (3×60 mL), and dried in vacuum oven at 70° C. to afford compound 20 in 45.6% (3.80 g) yield as a yellow solid. $^1$H-NMR (DMSO-$d_6$, 400 MHz) δ 9.95 (1H, s, OH), 9.87 (1H, s, CHO), 7.35 (1H, d, J=8.4 Hz, Ar), 7.11 (1H, d, J=8.4 Hz, Ar), 3.88 (3H, s, $OCH_3$); $^{13}$C-NMR (DMSO-$d_6$, 100 MHz) δ 195.1, 152.5, 146.8, 128.7, 123.3, 111.4, 91.5, 56.8; MS (ESI) m/z Calcd for $C_8H_7IO_3$ ($M^+$): 277.9, Found: 278.9 ($M+H^+$).

Example 16

3,4-Dihydroxybenzaldehyde (Compound 21)

To a stirred suspension of compound 20 (1.20 g, 4.32 mmol) in $CH_2Cl_2$ (40 mL) was added $AlCl_3$ (691 mg, 5.18 mmol) gradually over a period of 5 min. Pyridine (1.53 mL, 19.01 mmol) was then added dropwise to the vigorously stirred mixture. The reaction mixture was refluxed for 20 h, then cooled to 0° C., and acidified to pH ~1 with 6 N aqueous HCl. TLC analysis revealed the precipitate was mostly the product, which was then dissolved in a minimum volume of acetone. The aqueous layer of the filtrate was separated and extracted with $Et_2O$ (3×80 mL). The $Et_2O$ extracts were combined with the acetone solution of the precipitate and the resulting mixture was diluted with $Et_2O$ (300 mL), and washed with 0.1 N aqueous HCl (3×30 mL). The organic layer was collected, dried over anhydrous $Na_2SO_4$, filtered, concentrated and dried under vacuum to afford compound 21 in 96.1% (1.10 g) yield as a yellow solid. $^1$H-NMR (DMSO-$d_6$, 400 MHz) δ 10.99 (1H, s, OH), 9.81 (1H, s, CHO), 9.63 (1H, s, OH), 7.24 (1H, d, J=8.4 Hz, Ar), 6.87 (1H, d, J=8.4 Hz, Ar); $^{13}$C-NMR (DMSO-$d_6$, 100 MHz) δ 194.9, 151.4, 146.1, 127.6, 123.6, 115.0, 92.7; MS (ESI) m/z Calcd for $C_7H_5IO_3$ ($M^+$): 263.9, Found: 264.9 ($M+H^+$).

Example 17

2-Iodo-3,4-diisobutoxybenzaldehyde (Compound 22)

$K_2CO_3$ (1.92 g, 13.92 mmol) was added to a solution of compound 21 (918 mg, 3.48 mmol) in DMF (20 mL), which was then stirred at room temperature for 30 min Isobutyl iodide (1.20 mL, 10.43 mmol) was added to the reaction mixture, and stirring was continued at 50° C. for 3 days. The reaction was diluted with $Et_2O$ (200 mL) and washed with $H_2O$ (3×50 mL), and brine. The organic layer was collected, dried over anhydrous $Na_2SO_4$, filtered, concentrated, and purified by silica column chromatography (8% EtOAc in hexanes) to afford compound 22 in 73.1% (955 mg) yield as a colorless oil. $^1$H-NMR (CDCl$_3$, 400 MHz) δ 10.01 (1H, s, CHO), 7.68 (1H, d, J=8.4 Hz, Ar), 6.93 (1H, d, J=8.4 Hz, Ar), 3.84 (2H, d, J=5.6 Hz, OCH$_2$), 3.78 (2H, d, J=5.6 Hz, OCH$_2$), 2.23-2.14 (2H, m, 2×C$\underline{H}$(CH$_3$)$_2$), 1.11 (6H, d, J=6.4 Hz, CH(C$\underline{H_3}$)$_2$), 1.08 (6H, d, J=6.4 Hz, CH(C$\underline{H_3}$)$_2$); $^{13}$C-NMR (CDCl$_3$, 100 MHz) δ 195.2, 157.3, 147.9, 128.6, 127.0, 112.3, 100.7, 79.1, 75.3, 29.2, 28.2, 19.4, 19.2; MS (ESI) m/z Calcd for $C_{15}H_{21}IO_3$ ($M^+$): 376.1, Found: 377.0 ($M+H^+$).

Example 18

Methyl 2-iodo-3,4-diisobutoxybenzoate (Compound 23)

To a solution of compound 22 (300 mg, 0.80 mmol) in acetone (8 mL) and $H_2O$ (4 mL) was added KMnO$_4$ (441 mg, 2.79 mmol) in portions over 12 h. The reaction mixture was stirred at room temperature for 24 h and then filtered over a pad of Celite, washed with $H_2O$ (50 mL) and acetone (50 mL). The organic solvent was removed by evaporation, and the aqueous layer was basified by adding 1 N aqueous NaOH (4.5 mL), and then washed with $Et_2O$ (3×20 mL). The aqueous layer was cooled to 0° C., acidified to pH ~2 with 3 N aqueous HCl, then extracted with EtOAc (4×30 mL). The combined organic layers were dried over anhydrous $Na_2SO_4$, filtered, concentrated, and dried under vacuum to afford 2-iodo-3,4-diisobutoxybenzoic acid in 82.3% (258 mg) yield as a brown solid. $^1$H-NMR (DMSO-$d_6$, 400 MHz) δ 12.86 (1H, s, CO$_2$H), 7.46 (1H, d, J=8.4 Hz, Ar), 7.06 (1H, d, J=8.4 Hz, Ar), 3.80 (2H, d, J=5.6 Hz, OCH$_2$), 3.65 (2H, d, J=5.6 Hz, OCH$_2$), 2.07-2.00 (2H, m, 2×CH(C$\underline{H_3}$)$_2$), 1.01 (6H, d, J=6.8 Hz, CH(C$\underline{H_3}$)$_2$), 0.98 (6H, d, J=6.8 Hz, CH(C$\underline{H_3}$)$_2$); $^{13}$C-NMR (DMSO-$d_6$, 100 MHz) δ 168.0, 154.1, 148.2, 129.4, 127.2, 113.0, 94.7, 78.5, 74.9, 29.1, 28.2, 19.7, 19.4; MS (ESI) m/z Calcd for $C_{15}H_{21}IO_4$ ($M^+$): 392.5, Found: 391.5 ($M-H^+$). The title compound 23 was prepared from 2-iodo-3,4-diisobutoxybenzoic acid (220 mg, 0.56 mmol), $K_2CO_3$ (116 mg, 0.84) and iodomethane (38 μL, 0.62 mmol) in a manner similar to that described for compound 11 in 99.5% (226 mg) yield as a colorless oil. $^1$H-NMR (CDCl$_3$, 400 MHz) δ 7.55 (1H, d, J=8.8 Hz, Ar), 6.83 (1H, d, J=8.8 Hz, Ar), 3.87 (3H, s, OCH$_3$), 3.77 (2H, d, J=6.0 Hz, OCH$_2$), 3.73 (2H, d, J=6.0 Hz, OCH$_2$), 2.20-2.11 (2H, m, 2×C$\underline{H}$(CH$_3$)$_2$), 1.08 (6H, d, J=5.6 Hz, CH(C$\underline{H_3}$)$_2$), 1.05 (6H, d, J=5.6 Hz, CH(C$\underline{H_3}$)$_2$); $^{13}$C-NMR (CDCl$_3$, 100 MHz) δ 166.7, 154.7, 148.8, 127.5, 127.4, 111.8, 94.8, 78.8, 75.1, 52.2, 29.1, 28.3, 19.4, 19.2; MS (ESI) m/z Calcd for $C_{16}H_{23}IO_4$ ($M^+$): 406.1, Found: 407.1 ($M+H^+$).

Example 19

Methyl 2-((2-amino-5-(benzyloxy)phenyl)ethynyl)-3,4-diisobutoxybenzoate (Compound 24)

The title compound 24 was prepared from compound 18 (177 mg, 0.60 mmol), compound 23 (188 mg, 0.46 mmol), copper (I) iodide (9 mg, 10 mol %), bis(triphenylphosphine)palladium(II)dichloride (32 mg, 10 mol %) and Et$_3$N (3 mL) in a manner similar to that described for compound 17 in 50.0% (147 mg) yield as a dark brown oil. $^1$H-NMR (CDCl$_3$, 400 MHz) δ 7.75 (1H, d, J=8.8 Hz, Ar), 7.42-7.28 (5H, m, Ar), 6.99 (1H, s, Ar), 6.85-6.80 (2H, m, Ar), 6.65 (1H, d, J=9.6 Hz, Ar), 4.97 (2H, s, OCH$_2$), 4.80 (2H, s, NH$_2$), 3.87 (5H, s, OCH$_2$+OCH$_3$), 3.79 (2H, d, J=5.6 Hz, OCH$_2$), 2.19-2.13 (2H, m, 2×C$\underline{H}$(CH$_3$)$_2$), 1.11 (6H, d, J=5.6 Hz, CH(C$\underline{H_3}$)$_2$), 1.06 (6H, d, J=5.6 Hz, CH(C$\underline{H_3}$)$_2$); $^{13}$C-NMR (CDCl$_3$, 100 MHz) δ 165.8, 155.8, 150.3, 149.8, 144.4, 137.3, 134.7, 128.4, 127.8, 127.4, 127.2, 122.9, 119.9, 119.0, 116.7, 115.4, 111.4, 108.1, 96.3, 89.4, 79.9, 75.0, 70.8, 51.9, 29.4, 28.3, 19.4, 19.2; MS (ESI) m/z Calcd for $C_{31}H_{35}NO_5$ ($M^+$): 501.2, Found: 501.1 ($M^+$).

Example 20 tert-Butyl (2-(2-((2-amino-5-(benzyloxy)phenyl)ethynyl)-3,4-diisobutoxybenzamido) ethyl)carbamate (Compound 25)

To a solution of 24 (100 mg, 0.20 mmol) in THF/MeOH/$H_2O$ (ratio=3:1:1, 3 mL) was added LiOH.H$_2$O (42 mg, 1.00 mmol). The reaction mixture was stirred at room temperature overnight. The reaction mixture was neutralized by adding 1M HCl (aq) and partitioned between EtOAc and sat'd NaH$_2$PO$_4$ (aq). The organic layer was collected, dried over Na$_2$SO$_4$, filtered, concentrated and dried under vacuum to afford 2-((2-Amino-5-(benzyloxy)phenyl)ethynyl)-3,4-diisobutoxybenzoic acid in 66.0% (64 mg) yield as a dark brown solid. $^1$H-NMR (DMSO-$d_6$, 400 MHz) δ 7.59-7.52 (5H, m, Ar), 7.35 (2H, m, NH$_2$), 7.28 (1H, m, Ar), 6.94 (1H, d, J=8.0 Hz, Ar), 6.77 (1H, d, J=6.8 Hz, Ar), 6.68 (1H, s, Ar), 6.59 (1H, d, J=8.0 Hz, Ar), 4.92 (2H, s, OCH$_2$), 3.75-3.74 (4H, m, 2×OCH$_2$), 2.03-2.01 (2H, m, 2×C$\underline{H}$(CH$_3$)$_2$), 1.02 (6H, d, J=5.2 Hz, CH(C$\underline{H_3}$)$_2$), 0.99 (6H, d, J=6.0 Hz, CH(C$\underline{H_3}$)$_2$); $^{13}$C-NMR (DMSO-$d_6$, 100 MHz) δ 148.8, 148.5, 146.7, 138.1, 133.6, 132.6, 132.5, 132.0, 131.9, 129.4, 129.3, 128.7, 128.5, 128.3, 127.6, 127.0, 119.1, 116.4, 114.8, 112.3, 106.3, 79.8, 75.1, 70.4, 29.4, 28.3, 19.8, 19.6; MS (ESI) m/z Calcd for $C_{30}H_{33}NO_5$ ($M^+$): 487.2, Found: 486.2 ($M-H^+$). The title compound 25 was prepared from 2-((2-amino-5-(benzyloxy)phenyl)ethynyl)-3,4-diisobutoxybenzoic acid (56 mg, 0.11 mmol), N-Boc-ethylenediamine (73 mg, 0.46 mmol), HBTU (63 mg, 0.17 mmol) and DIPEA (77 μL, 0.44 mmol) in a manner similar to that described for compound 2 in 87.0% (60 mg) yield as a yellow oil. $^1$H-NMR (CDCl$_3$, 400 MHz) δ 7.69-7.64 (3H, m, Ar), 7.54-7.50 (2H, m, Ar), 7.46 (2H, m, NH$_2$), 7.41-7.36 (3H, m, Ar), 7.33 (1H, d, J=7.2 Hz, Ar), 6.94 (1H, s, Ar), 6.87 (1H, d, J=8.8 Hz, Ar), 6.69 (1H, d, J=8.8 Hz, Ar), 4.99 (2H, s, OCH$_2$), 3.87 (2H, d, J=5.6 Hz, OCH$_2$), 3.78 (2H, d, J=5.6 Hz, OCH$_2$), 3.53 (2H, m, NHC H₂CH₂), 3.34 (2H, m, NHCH₂CH₂), 2.15-2.13 (2H, m, 2×CH(CH₃)₂), 1.36 (9H, s, C(CH₃)₃), 1.07 (12H, d, J=5.6 Hz, 2×CH(CH₃)₂); ¹³C-NMR (CDCl₃, 100 MHz) δ 167.7, 156.6, 154.2, 150.9, 149.7, 143.1, 137.2, 133.0, 132.1, 132.0, 131.9, 128.7, 128.5, 128.4, 127.8, 127.4, 124.7, 119.0, 116.6, 116.2, 116.0, 112.5, 112.2, 108.0, 95.8, 89.2, 40.6, 40.5, 29.6, 29.3, 28.3, 28.2, 19.4, 19.2; MS (ESI) m/z Calcd for $C_{37}H_{47}N_3O_6$ (M⁺): 629.3, Found: 629.4 (M⁺).

Example 21

Ethyl 2-(4-(benzyloxy)-2-((6-(2-((tert-butoxycarbonyl)amino)ethyl)carbamoyl)-2,3-diisobutoxyphenyl)ethynyl)phenyl)amino)-2-oxoacetate (Compound 26)

To an ice-cooled solution of compound 25 (60 mg, 0.10 mmol) and Et₃N (21 μL, 0.15 mmol) in CH₂Cl₂ (2 mL) was added dropwise a solution of ethyl chlorooxoacetate (14 μL, 0.12 mmol) in CH₂Cl₂ (1 mL). The reaction mixture was stirred at room temperature for 1 h and then partitioned between CH₂Cl₂ and H₂O. The organic layer was washed with brine, dried over anhydrous Na₂SO₄, filtered, concentrated and purified by silica gel column chromatography (30% EtOAc in hexanes) to afford compound 26 in 52.0% (38 mg) yield as a yellow solid. ¹H-NMR (CDCl₃, 400 MHz) δ 9.69 (1H, s, NH), 8.38 (1H, d, J=9.2 Hz, Ar), 7.49 (1H, d, J=8.0 Hz, Ar), 7.42-7.32 (6H, m, Ar+NH), 7.12 (1H, d, J=2.4 Hz, Ar), 7.07 (1H, t, J=4.8 Hz, NH), 7.03 (1H, dd, J=2.4 Hz, 9.2 Hz, Ar), 6.90 (1H, d, J=9.2 Hz, Ar), 5.06 (2H, s, OCH₂), 4.35 (2H, q, J=7.2 Hz, OCH₂CH₃), 3.87 (2H, d, J=6.4 Hz, OCH₂), 3.77 (2H, d, J=6.4 Hz, OCH₂), 3.47 (2H, m, NHCH₂CH₂), 3.28 (2H, m, NHCH₂CH₂), 2.13 (1H, sep, J=6.4 Hz, CH(CH₃)₂), 2.04 (1H, sep, J=6.4 Hz, CH(CH₃)₂), 1.35 (9H, s, C(CH₃)₃), 1.32 (3H, t, J=7.2 Hz, OCH₂CH₃), 1.06 (6H, d, J=6.4 Hz, CH(CH₃)₂), 1.00 (6H, d, J=6.4 Hz, CH(CH₃)₂); ¹³C-NMR (CDCl₃, 100 MHz) δ 167.2, 160.7, 156.6, 155.3, 154.8, 154.2, 150.3, 136.4, 131.7, 129.4, 128.6, 128.0, 127.4, 124.6, 121.4, 117.1, 115.1, 114.2, 113.2, 92.5, 91.1, 80.0, 79.4, 75.1, 70.3, 63.2, 40.8, 40.4, 29.2, 28.3, 28.2, 19.2, 13.8; MS (ESI) m/z Calcd for $C_{41}H_{51}N_3O_9$ (M⁺): 729.4, Found: 730.3 (M+H⁺).

Example 22

2-((2-((6-((2-Aminoethyl)carbamoyl)-2,3-diisobutoxyphenyl)ethynyl)-4-(benzyloxy)phenyl)amino)-2-oxoacetic acid (14)

Compound 2-((4-(benzyloxy)-2-((6-((2-((tert-butoxycarbonyl)amino)ethyl)carbamoyl)-2,3-diisobutoxyphenyl)ethynyl)phenyl)amino)-2-oxoacetic acid (Boc-protected 14) was prepared from compound 26 (38 mg, 0.052 mmol) and LiOH.H₂O (2.0 mg, 0.052 mmol) in a manner similar to that described for compound 13 in 99.5% (36 mg) yield as a light yellow solid. ¹H-NMR (DMSO-d₆, 400 MHz) δ 9.96 (1H, s, NH), 8.22 (1H, s, NH), 8.09 (1H, d, J=8.0 Hz, Ar), 7.40-7.30 (6H, m, Ar+NH), 7.12-7.06 (3H, m, Ar), 6.77-6.73 (1H, m, Ar), 5.09 (2H, s, OCH₂), 3.80 (4H, m, 2×OCH₂), 3.20 (2H, m, NHCH₂CH₂), 3.02 (2H, m, NHCH₂CH₂), 2.03-2.01 (1H, m, CH(CH₃)₂), 1.95-1.94 (1H, m, CH(CH₃)₂), 1.30 (9H, s, C(CH₃)₃), 0.99 (6H, d, J=5.2 Hz, CH(CH₃)₂), 0.92 (6H, d, J=6.4 Hz, CH(CH₃)₂); ¹³C-NMR (CDCl₃, 100 MHz) δ 167.8, 167.5, 163.0, 161.4, 158.3, 157.0, 156.4, 155.6, 154.2, 153.9, 150.2, 136.4, 131.2, 128.9, 128.6, 128.1, 127.4, 124.5, 121.6, 117.2, 117.0, 115.3, 115.1, 113.1, 92.4, 91.2, 81.9, 80.0, 75.0, 70.3, 40.7, 40.1, 29.2, 28.3, 28.2, 19.3, 19.2; MS (ESI) m/z Calcd for $C_{39}H_{47}N_3O_9$ (M⁺): 701.3, Found: 701.2 (M⁺). To a solution of 2-((4-(benzyloxy)-2-((6-((2-((tert-butoxycarbonyl)amino)ethyl)carbamoyl)-2,3-diisobutoxyphenyl)ethynyl)phenyl)amino)-2-oxoacetic acid (Boc-protected 14; 32 mg, 0.046 mmol) in CH₂Cl₂ (1 mL) was added 20% TFA in CH₂Cl₂ (1 mL) and the reaction solution was stirred at room temperature for 30 min. The reaction solvent and TFA were removed by evaporation. Residual TFA was removed by co-evaporation with toluene (×3). The product was purified by prep-TLC using CH₂Cl₂/MeOH/H₂O (ratio=62:25:4) to afford compound 14 in 60.0% (16 mg) yield as a white solid. ¹H-NMR (DMSO-d₆, 400 MHz) δ 9.94 (1H, s, NH), 8.34 (3H, bs, NH₂+NH), 8.25 (1H, d, J=8.8 Hz, Ar), 7.39-7.36 (5H, m, Ar), 7.31 (1H, d, J=6.0 Hz, Ar), 7.15 (1H, d, J=8.8 Hz, Ar), 7.07 (1H, d, J=8.8 Hz, Ar), 6.97 (1H, s, Ar), 5.07 (2H, s, OCH₂), 3.82 (2H, d, J=4.8 Hz, OCH₂), 3.79 (2H, d, J=4.8 Hz, OCH₂), 3.50 (2H, m, NHCH₂CH₂), 2.93 (2H, m, NHCH₂CH₂), 2.03-2.01 (2H, m, 2×CH(CH₃)₂), 0.98 (12H, d, J=3.2 Hz, 2×CH(CH₃)₂); ¹³C-NMR (DMSO-d₆, 100 MHz) δ 166.6, 165.2, 154.1, 154.0, 149.9, 137.2, 134.2, 129.4, 128.9, 128.3, 127.9, 124.6, 121.0, 117.3, 116.8, 116.3, 113.8, 113.6, 93.0, 91.1, 79.7, 74.9, 69.9, 38.7, 37.6, 29.4, 29.3, 28.2, 19.6, 19.4; MS (ESI) m/z Calcd for $C_{34}H_{39}N_3O_7$ (M⁺): 601.3, Found: 624.2 (M+Na⁺).

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

REFERENCES

1. D. J. Barlow and J. M. Thornton, *J. Mol. Biol.*, 1988, 201, 601.
2. S. Fletcher and A. D. Hamilton, *Curr. Opin. Chem. Biol.*, 2005, 9, 632.
3. B. N. Bullock, A. L. Jochim, P. S. Arora, *J. Am. Chem. Soc.*, 2011, 133, 14220.
4. J. P. Schneider and J. W. Kelly, *Chem. Rev.*, 1995, 95, 2169.
5. S. Marqusee and R. L. Baldwin, *Proc. Natl. Acad. Sci. USA*, 1987, 84, 8898.
6. M. Bouvier and J. W. Taylor, *J. Med. Chem.*, 1992, 35, 1145.
7. D. Y. Jackson, D. S. King, J. Chmielewski, S. Singh, P. G. Shultz, *J. Am. Chem. Soc.*, 1991, 113, 9391.
8. C. E. Schafineister, J. Po and G. L. Verdine, *J. Am. Chem. Soc.*, 2000, 122, 5891.
9. S. W. Horne and S. H. Gellman, *Acc. Chem. Res.*, 2008, 41, 3199.
10. (a) C. G. Cummings and A. D. Hamilton, *Curr. Opin. Chem. Biol.*, 2010, 14, 341. (b) V. Azzarito, K. Long, N. S. Murphy, A. J. Wilson, *Nat. Chem.*, 2013, 5, 161.
11. J. T. Ernst, O. Kutzki, A. K. Debnath, S. Jiang, H. Lu and A. D. Hamilton, *Angew. Chem. Int. Ed.*, 2002, 41, 278.
12. J. M. Davis, Truong, A. and A. D. Hamilton, *Org. Lett.*, 2005, 7, 5405.
13. H. Yin, G. I. Lee, H. S. Park, G. A. Payne, J. M. Rodriguez, S. M. Sebti and A. D. Hamilton, *J. Am. Chem. Soc.*, 2005, 127, 5463.
14. J. T. Ernst, J. Becerril, H. S. Park, H. Yin and A. D. Hamilton, *Angew. Chem. Int. Ed.*, 2003, 42, 535.

15. J. Plante, F. Campbell, B. Malkova, C. Kilner, S. L. Warriner and A. J. Wilson, *Org. Biomol. Chem.*, 2008, 6, 138.
16. Yap, J. L., X. Cao, K. Vanommeslaeghe, K.-Y. Jung, C. Peddaboina, P. T. Wilder, A. Nan, A. D. MacKerell, Jr., W. R. Smythe and S. Fletcher, *Org. Biomol. Chem.*, 2012, 10, 2928.
17. (a) A. Volonterio, L. Moisan and J. Rebek, Jr., *Org. Lett.*, 2007, 9, 3733; (b) C. G. Cummings, N. T. Ross, W. P. Katt and A. D. Hamilton, *Org. Lett.*, 2009, 11, 25.
18. J. L. Cornette, K. B. Cease, H. Margalit, J. L. Spouge, J. A. Berzofsky and Charles DeLisi, *J. Mol. Biol.*, 1987, 195, 695.
19. (a) S. Marimganti, M. N. Cheemala and J.-M. Ahn, *Org. Lett.*, 2009, 11, 4418; (b) S. Thompson, R. Vallinayagam, M. J. Adler, R. T. W. Scott and A. D. Hamilton, *Tetrahedron*, 2012, 68, 4501.
20. J. M. Cary and J. S. Moore, *Org. Lett.*, 2002, 4, 4663.
21. P. N. Wyrembak and A. D. Hamilton, *J. Am. Chem. Soc.*, 2009, 131, 4566.
22. (a) J. M. Adams and S. Cory, *Science*, 1998, 281, 1322; (b) R. J. Youle and A. Strasser, *Nat. Rev. Mol. Cell. Biol.*, 2008, 9, 47.
23. A. Jansma, Q. Zhang, B. Li, Q. Ding, T. Uno, B. Bursulaya, Y. Liu, P. Furet, N. S. Gray, B. H. Geierstanger, *J. Med. Chem.* 2007, 50, 5875.
24. G. Wagner, A. Pardi, K. Wuethrich, *J. Am. Chem. Soc.*, 1983, 105, 5948.
25. B. R. Brooks, C. L. Brooks, III, A. D. MacKerell, Jr., L. Nilsson, R. J. Petrella, B. Roux, Y. Won, G. Archontis, C. Bartels, S. Boresch, A. Caflisch, L. Caves, Q. Cui, A. R. Dinner, M. Feig, S. Fischer, J. Gao, M. Hodošček, W. Im, K. Kuczera, T. Lazaridis, J. Ma, V. Ovchinnikov, E. Paci, R. W. Pastor, C. B. Post, J. Z. Pu, M. Schaefer, B. Tidor, R. M. Venable, H. L. Woodcock, X. Wu, W. Yang, D. M. York and M. Karplus, *J. Comput. Chem.* 2009, 30, 1545.
26. K. Vanommeslaeghe, E. Hatcher, C. Acharya, S. Kundu, S. Zhong, J. Shim, E. Darian, O. Guvench, P. Lopes, I. Vorobyov, A. D. MacKerell Jr., *J. Comput. Chem.*, 2010, 31, 671.
27. K. Vanommeslaeghe, A. D. MacKerell Jr., *J. Chem. Inf. Model.*, 2012, 52, 3144.
28. K. Vanommeslaeghe, E. P. Raman, A. D. MacKerell Jr., *J. Chem. Inf. Model.*, 2012, 52, 3155.
29. M. P. Allen, D. J. Tildesley, *Computer Simulation of Liquids*; Clarendon Press: Oxford, 1987.
30. T. A. Darden, D. York, L. G. Pedersen, *J. Chem. Phys.*, 1993, 98, 10089.
31. P. J. Steinbach, B. R. Brooks, *J. Comput. Chem.*, 1994, 15, 667.
32. R. W. Hockney, In *Methods in Computational Physics*; B. Alder, S. Fernbach, M. Rotenberg, Eds.; Academic Press: New York, 1970, p 136-211.
33. J. P. Ryckaert, G. Ciccotti, H. J. C. Berendsen, *J. Comput. Phys.*, 1977, 23, 327.
34. S, Nosé, Mol. Phys., 1984, 52, 255.
35. W. G. Hoover, *Phys. Rev. A,* 1985, 31, 1695.
36. S. E. Feller, Y. Zhang, R. W. Pastor, B. R. Brooks, *J. Chem. Phys.*, 1995, 103, 4613.
37. (a) M. D. Boersma, J. D. Sadowsky, Y. A. Tomita and S. H. Gellman, *Protein Sci.*, 2008, 17, 1232; (b) Z. Zhang, X. Li, T. Song, Y. Zhao and Y. Feng, *J. Med. Chem.* 2012, 55, 10735.
38. P. E. Czabotar, E. F. Lee, M. F. van Delft, C. L. Day, B. J. Smith, D. C. S. Huang, W. D. Fairlie, M. G. Hinds and P. M. Colman, *Proc. Natl. Acad. Sci. USA* 2007, 104, 6217.

What is claimed is:
1. A compound of formulas 1a-1c:

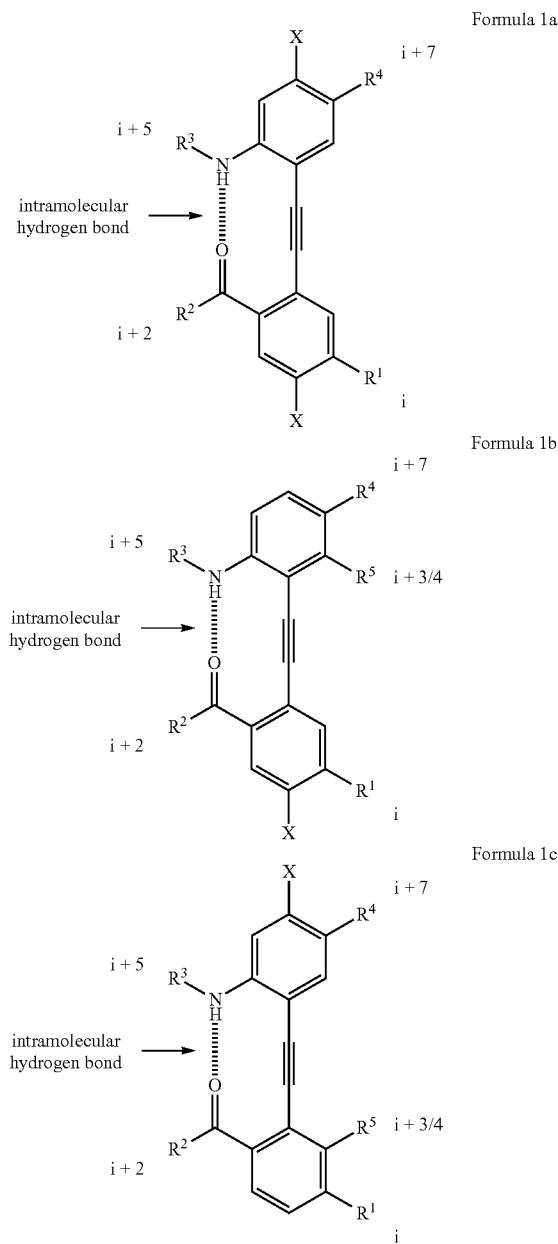

wherein:
$R^1$, $R^4$ and $R^5$ can be alkyl, cycloalkyl, alkenyl, alkynyl, aryl, $CH_2$-aryl, heteroaryl, $CH_2$-heteroaryl, $CH_2CO_2H$, $CH_2CH_2CO_2H$, $CH_2OH$, $(CH_2)_4NH_2$, $(CH_2)_3N=C(NH_2)_2$, O-alkyl, O-cycloalkyl, O-alkenyl, O-alkynyl, O-aryl, O—$CH_2$-aryl, O-heteroaryl, O—$CH_2$-heteroaryl, O—$CH_2CO_2H$, O—$CH_2CH_2CO_2H$, O—$(CH_2)_2OH$, O—$(CH_2)_4NH_2$, or O—$(CH_2)_3N=C(NH_2)_2$;

$R^2$ can be alkyl, cycloalkyl, alkenyl, alkynyl, aryl, $CH_2$-aryl, heteroaryl, $CH_2$-heteroaryl, O-alkyl, O-cycloalkyl, O-alkenyl, O-alkynyl, O-aryl, O—$CH_2$-aryl, O-heteroaryl, O—$CH_2$-heteroaryl, NH-alkyl, NH-cycloalkyl, NH-alkenyl, NH-alkynyl, NH-aryl, NH—$CH_2$-aryl, NH-heteroaryl, NH—CH$_2$-heteroaryl, CO-alkyl, CO-cycloalkyl, CO-alkenyl, CO-alkynyl, CO-aryl, CO—CH$_2$-aryl, CO-heteroaryl, CO—CH$_2$-heteroaryl, CO$_2$-alkyl, CO$_2$-cycloalkyl, CO$_2$-alkenyl, CO$_2$-alkynyl, CO$_2$-aryl, CO$_2$—CH$_2$-aryl, CO$_2$-heteroaryl, or CO$_2$—CH$_2$-heteroaryl;

R$^3$ can be alkyl, cycloalkyl, alkenyl, alkynyl, aryl, CH$_2$-aryl, heteroaryl, CH$_2$-heteroaryl, CO-alkyl, CO-cycloalkyl, CO-alkenyl, CO-alkynyl, CO-aryl, CO—CH$_2$-aryl, CO-heteroaryl, CO—CH$_2$-heteroaryl, CO$_2$-alkyl, CO$_2$-cycloalkyl, CO$_2$-alkenyl, CO$_2$-alkynyl, CO$_2$-aryl, CO$_2$—CH$_2$-aryl, CO$_2$-heteroaryl, CO$_2$—CH$_2$-heteroaryl, COCO$_2$H, COCO$_2$-alkyl, COCO$_2$-cycloalkyl, COCO$_2$-alkenyl, COCO$_2$-alkynyl, COCO$_2$-aryl, COCO$_2$—CH$_2$-aryl, COCO$_2$-heteroaryl, COCO$_2$—CH$_2$-heteroaryl, SO$_2$-alkyl, SO$_2$-cycloalkyl, SO$_2$-alkenyl, SO$_2$-alkynyl, SO$_2$-aryl, SO$_2$—CH$_2$-aryl, SO$_2$-heteroaryl, or SO$_2$—CH$_2$-heteroayl; and X=H or OCH$_2$CO$_2$H, wherein the latter functionality serves as a solubilizing group.

2. The compound of claim 1, comprising a compound of formula 1a, wherein R$^1$ and R$^4$ are the same as or different from one another and are selected from the group consisting of O-alkyl, O-cycloalkyl, O-alkenyl, O-alkynyl, O-aryl, O—CH$_2$-aryl, O-heteroaryl, O—CH$_2$-heteroaryl, O—CH$_2$CO$_2$H, O—CH$_2$CH$_2$CO$_2$H, O—(CH$_2$)$_2$OH, O—(CH$_2$)$_4$NH$_2$, and O—(CH$_2$)$_3$N=C(NH$_2$)$_2$, R$^2$ is selected from the group consisting of NH-alkyl, NH-cycloalkyl, NH-alkenyl, NH-alkynyl, NH-aryl, NH—CH$_2$-aryl, NH-heteroaryl, and NH—CH$_2$-heteroaryl, R$^3$ is selected from the group consisting of CO-alkyl, CO-cycloalkyl, CO-alkenyl, CO-alkynyl, CO-aryl, CO—CH$_2$-aryl, CO-heteroaryl, CO—CH$_2$-heteroaryl, CO$_2$-alkyl, CO$_2$-cycloalkyl, CO$_2$-alkenyl, CO$_2$-alkynyl, CO$_2$-aryl, CO$_2$—CH$_2$-aryl, CO$_2$-heteroaryl, CO$_2$—CH$_2$-heteroaryl, COCO$_2$H, COCO$_2$-alkyl, COCO$_2$-cycloalkyl, COCO$_2$-alkenyl, COCO$_2$-alkynyl, COCO$_2$-aryl, COCO$_2$—CH$_2$-aryl, COCO$_2$-heteroaryl, and COCO$_2$—CH$_2$-heteroaryl, and X is H.

3. The compound of claim 1, comprising a compound of formula 2:

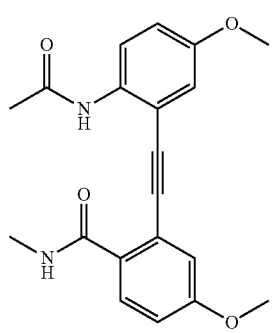

Formula 2

4. The compound of claim 1, comprising a compound of formula 14:

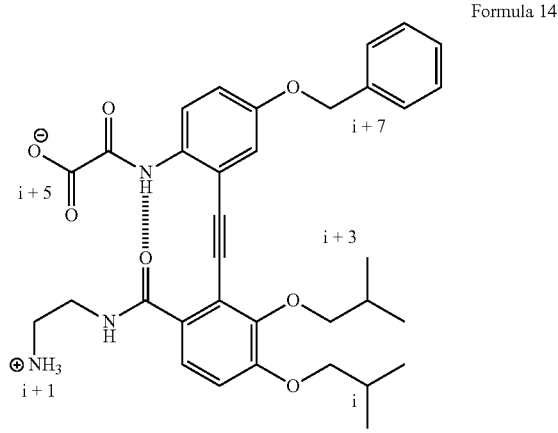

Formula 14

5. A method of disrupting disease-promoting protein-protein interactions that are mediated by α-helices, said method comprising interacting a compound of claim 1 with a protein such that the protein-protein interactions are antagonized and the disease promotion is disrupted, wherein the disease-promoting protein-protein interactions are selected from the group consisting of Bim-Mcl-1, c-Myc-Max, c-Jun-Fos, and p53-HDM2.

6. The method of claim 5, comprising interacting a compound of formula 2 with a protein such that the protein-protein interactions are antagonized and the disease promotion is disrupted.

7. The method of claim 5, comprising interacting a compound of formula 14 with a protein such that the protein-protein interactions are antagonized and the disease promotion is disrupted.

8. The method of claim 7, wherein the protein-protein interaction is Bim-Mcl-1.

9. A pharmaceutical composition comprising a compound of claim 1 and a pharmaceutically acceptable excipient.

10. The pharmaceutical formulation of claim 9, comprising a compound of formula 2.

11. The pharmaceutical formulation of claim 9, comprising a compound of formula 14.

* * * * *

UNITED STATES PATENT AND TRADEMARK OFFICE
CERTIFICATE OF CORRECTION

PATENT NO. : 8,901,164 B2
APPLICATION NO. : 14/200774
DATED : December 2, 2014
INVENTOR(S) : Steven Fletcher It is certified that error appears in the above-identified patent and that said Letters Patent is hereby corrected as shown below:

On the Title page,

Item (74) Attorney, Agent, or Firm, - "Marianne Fuierer" should be -- Tristan Anne Fuierer --

Replace Item (57) Abstract with:

Small-molecule scaffolds based on 1,2-diphenylacetylene that accurately replicate the spatial and angular projections of several side chains on both faces of an α-helix, specifically the i and i + 7 side chains on one face, and the i+5 and i + 2 side chains on the other. The amphipathic α-helix mimetic can be used to disrupt disease-promoting protein-protein interactions that are mediated by α-helices.

In the Specification,

Column 2, line 16, "i+7 side chains on one face, and the i and" should be -- i+7 side chains on one face, and the i+5 and --

Column 4, line 66, "i+7 side chains on one face, and the i and" should be -- i+7 side chains on one face, and the i+5 and --

Signed and Sealed this
Second Day of June, 2015

Michelle K. Lee
*Director of the United States Patent and Trademark Office*